(12) United States Patent
Skibsted et al.

(10) Patent No.: US 12,233,114 B2
(45) Date of Patent: *Feb. 25, 2025

(54) METHOD FOR TREATING DIABETES

(71) Applicant: Novo Nordisk A/S, Bagsvaerd (DK)

(72) Inventors: Simon Skibsted, Princeton, NJ (US); Kajsa Kvist, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 379 days.

This patent is subject to a terminal disclaimer.

(21) Appl. No.: 17/667,223

(22) Filed: Feb. 8, 2022

(65) Prior Publication Data

US 2022/0160840 A1    May 26, 2022

Related U.S. Application Data

(63) Continuation of application No. 16/463,598, filed as application No. PCT/EP2017/080600 on Nov. 28, 2017, now Pat. No. 11,278,596.

(30) Foreign Application Priority Data

Nov. 28, 2016  (EP) ..................................... 16200906
Jun. 7, 2017   (EP) ..................................... 17174682

(51) Int. Cl.
    A61K 38/28    (2006.01)
    A61P 3/10     (2006.01)
    A61P 9/00     (2006.01)

(52) U.S. Cl.
    CPC ............... *A61K 38/28* (2013.01); *A61P 3/10* (2018.01); *A61P 9/00* (2018.01)

(58) Field of Classification Search
    CPC ............... A61K 38/28; A61P 3/10; A61P 9/00
    See application file for complete search history.

(56) References Cited

U.S. PATENT DOCUMENTS

| | | | |
|---|---|---|---|
| 2016/0058840 A1 | 3/2016 | Johansen et al. | |
| 2019/0374614 A1 | 12/2019 | Skibsted et al. | |
| 2020/0181222 A1 | 6/2020 | Christensen | |

FOREIGN PATENT DOCUMENTS

| | | | |
|---|---|---|---|
| WO | 2004064862 A1 | 8/2004 | |
| WO | 2013144273 A1 | 10/2013 | |
| WO | 2014147141 A1 | 9/2014 | |
| WO | 2014177623 A1 | 11/2014 | |

OTHER PUBLICATIONS

Ahmann et al., "Efficacy and safety of Liraglutide Versus Placebo Added to Basal Insulin Analogues (with or without metformin) in Patients with Type 2 Diabetes: a Randomized, Placebo-Controlled Trial," Diabetes. Obesity and Metabolism, 2015, vol. 17, No. 11, pp. 1056-1064.

Einhorn et al., "Patients Achieving Good Glycemic Control (HBA1c <7%) Experience a Lower Rate of Hypoglycemia With Insulin Degludec Than With Insulin Glargine: a Meta-Analysis of Phase 3A Trials," Endocrine Practice : Official Journal of the American College of Endocrinology and the American Association of Clinical Endocrinologists, AACE, USA, 2015, vol. 21, No. 8, pp. 917-926.
Freemantle et al., "IDegLira Versus Alternative Intensification Strategies in Patients with Type 2 Diabetes Inadequately Controlled on Basal Insulin Therapy," Diabetes Therapy, 2015, vol. 6, No. 4, pp. 573-591.
Melzer et al., "Real Life Data Demonstrate Significant Reductions In HBA1C In T2DM Patients Switching From Other Insulins To Insulin Degludec," Value in Health, 2016, vol. 19, No. 7, p. A666.
Nagai et al., "Efficacy and Safety of Thrice-Weekly Insulin Degludec in Elderly Patients with Type 2 Diabetes Assessed by Continuous Glucose Monitoring," The Japan Endocrine Society, 2016, vol. 63, No. 12, pp. 1099-1106.
Novo Nordisk: "Insulin Degludec and Insulin Degludec/Insulin Aspart Treatment to Improve Glycemic Control in Patients with Diabetes Mellitus NDAs 203314 and 203313 Briefing Document," Nov. 8, 2012 (Nov. 8, 2012), XP055358223, Retrieved from the Internet: URL:https://www.fda.gov/downloads/AdvisoryCommittees/CommitteesMeetingMaterials/Drugs/EndocronologicandMetabolicDrugsAdvisoryCommittee/UCM327017.pdf, retrieved on Mar. 23, 2017.
Stratton et al., "Association of Glycaemia with Macrovascular and Microvascular Complications of Type 2 Diabetes (UKPDS 35): Prospective Observational Study", BMJ, 2000, vol. 321, No. 7258, pp. 405-412.
Kaku et al., "Safety, efficacy, and early clinical experience of insulin degludec in Japanese people with diabetes mellitus: A first-year report from Japan," J Diabetes Investig, 2015, vol. 6, pp. 610-619.
Wada et al., "Effects of long-acting insulin degludec on type 2 diabetic hemodialysis patients with poor glycemic control," 2015 PubMed, vol. 57, pp. 872-877, abstract (8 pages).
Aboyans et al., "AHA Scientific Statement, Measurement and Interpretation of the Ankle-Brachia! Index, A Scientific Statement From the American Heart Association", American Heart Association, Dec. 11, 2012, pp. 2890-2909.
Shamsham et al., "Essentials of the diagnosis of heart failure", American Family Physician, Mar. 1, 2000, vol. 61, No. 5, pp. 1319-1328.
Caudron et al., "Evaluation of left ventricular diastolic function with cardiac MR imaging", Radiographics, Jan.-Feb. 2011, vol. 31, No. 1, pp. 239-259.
Prakash et al., "Left ventricular hypertrophy in hypertension: Correlation between electrocardiogramand echocardiography", Kathmandu University Medical Journal, Feb. 2010, vol. 7, No. 2, pp. 97-103.
Chapter 1: Definition and classification of CKD, Kidney International Supplements, Jan. 2013, vol. 3, No. 1, pp. 19-62.
American Diabetes Association: Standards of Medical Care in Diabetes 2017 (Diabetes Care, Jan. 2017, vol. 40, Supplement 1).
Marso et al., "Design of DEVOTE (Trial Comparing Cardiovascular Safety of Insulin Degludec vs Insulin Glargine in Patients With Type 2 Diabetes at High Risk of Cardiovascular Events)—DEVOTE 1", Am. Heart J., Sep. 2016, vol. 179, pp. 175-183.

(Continued)

*Primary Examiner* — Gyan Chandra
(74) *Attorney, Agent, or Firm* — Elizabeth A. Dingess-Hammond

(57) ABSTRACT

The present invention relates to insulin degludec for use in medicine.

15 Claims, 1 Drawing Sheet

(56) References Cited

OTHER PUBLICATIONS

Keiji Kubo, "A Study on The Combination Therapy of Insulin Glargine and Oral Hypoglycemic Agents", Progress in Medicine, 2008, vol. 28, No. 11, p. 2757-2761.
Sato, J., et al., "The Efficacy of Insulin Detemir Compared with NPH Insulin as an Intensive Insulin Treatment Regimen in Patients with Type 2 Diabetes Mellitus; Assessment for 18 Months Period", J. Japan Diabetes Soc., 2011, vol. 54, No. 5, p. 344-348.

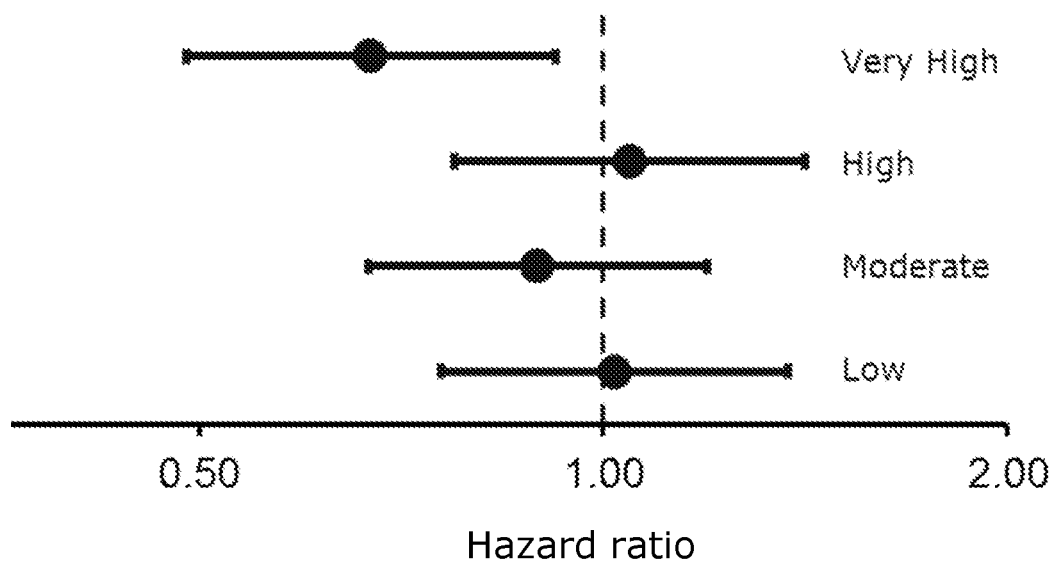

METHOD FOR TREATING DIABETES

CROSS-REFERENCE TO RELATED APPLICATIONS

This application is a continuation of U.S. application Ser. No. 16/463,598, filed May 23, 2019, which is a 35 U.S.C. § 371 National Stage application of International Application PCT/EP2017/080600 (WO 2018/096162), filed Nov. 28, 2017, which claims priority to European Patent Applications 16200906.2, filed Nov. 28, 2016 and 17174682.9, filed Jun. 7, 2017; the contents of which are incorporated herein by reference.

The present invention relates to the use of a basal insulin in cardiovascular conditions in a subject having at least diabetes.

BACKGROUND

Diabetes is a metabolic disorder characterized by hyperglycaemia that is associated with a high risk of cardiovascular and other serious health-related consequences. A person with diabetes is two to three times more likely to die from cardiovascular causes than people with no history of diabetes, even after controlling for other cardiovascular risk factors. They are also at very high risk of developing serious microvascular complications ultimately leading to premature death: nephropathy and renal failure, retinal disease and blindness, autonomic and peripheral neuropathy, as well as other conditions related to the vascular system: hypertension, lower limb amputation, cognitive decline, and erectile dysfunction.

The majority of people with diabetes have type 2 diabetes, which is characterised by insulin resistance and eventually impaired insulin secretion. Optimal glycaemic control is the treatment goal in subjects with type 2 diabetes, since the risk of long-term complications is increased with poor glycaemic control. Despite the availability of several oral and injectable anti-diabetic drugs, a significant proportion of subjects with type 2 diabetes do not achieve the recommended target levels. With the increasing incidence and prevalence of type 2 diabetes, there is an unmet medical need for treatment alternatives with improved efficacy, safety and convenience. With the availability of several basal insulins for the treatment of diabetes there is a need for treatment schemes such that the individual person with diabetes receives the treatment which maximizes treatment efficacy and minimizes known diabetes complications.

WO2013/144273 discloses that administration of a long acting insulin may reduce the risk of a new angina or the risk of a microvascular event in a patient diagnosed with impaired fasting glucose, impaired glucose tolerance or type 2 diabetes.

SUMMARY

In some embodiments the present invention relates to a method for treating diabetes, comprising administration of a basal insulin in a therapeutically effective amount to a subject in need thereof, wherein said subject has a cardiovascular disease or is at risk of developing a cardiovascular disease and wherein said basal insulin is insulin degludec, and wherein said method delays or reduces major adverse cardiovascular event (MACE).

In some embodiments the present invention relates to a method for treating diabetes, comprising administration of a basal insulin in a therapeutically effective amount to a subject in need thereof, wherein said subject has a cardiovascular disease or is at risk of developing a cardiovascular disease and wherein said subject is a female, has substantially Asian origin, and/or has substantially African origin, wherein said basal insulin is insulin degludec, and wherein said method delays or reduces major adverse cardiovascular event (MACE).

In some embodiments the present invention relates to the method wherein said subject has
  (i) one or more vascular disease selected from the group consisting of cardiovascular disease, cerebrovascular disease, peripheral vascular disease, chronic renal failure, and chronic heart failure, and/or
  (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9.

In some embodiments the present invention relates to a kit of parts comprising
  insulin degludec,
  a packaging material, and
  a label or package insert contained within the packaging material indicating that subjects receiving the treatment with insulin degludec can be treated by a method according to the present invention.

It has surprisingly been found that insulin degludec provides insulin therapy which has an improved outcome for the subjects being treated with respect to time to first MACE.

It has surprisingly also been found that subjects having diabetes which are female subjects, subjects having Asian origin or subjects having African origin all lower hazard ratios significantly when treated with insulin degludec as compared to placebo which is insulin glargine. The present invention allows for prescribing an optimal treatment with a basal insulin to said subjects.

BRIEF DESCRIPTION OF THE DRAWINGS

FIG. 1. Estimated hazard ratio by CV risk score in quartiles.

DESCRIPTION

In some embodiments the present invention relates to a method for treating diabetes, comprising administration of a basal insulin in a therapeutically effective amount to a subject in need thereof, wherein said subject has a cardiovascular disease or is at risk of developing a cardiovascular disease and wherein said subject is a female, has substantially asian origin, and/or has substantially african origin, wherein said basal insulin is insulin degludec, and wherein said method delays or reduces major adverse cardiovascular event (MACE).

The term "MACE" as used herein refers to major adverse cardiovascular event. In some embodiments MACE is events selected from the group consisting of cardiovascular (CV) death, non-fatal MI, non-fatal stroke, coronary revascularisation, hospitalisation for unstable angina pectoris, and hospitalisation for chronic heart failure. In some embodiments MACE is cardiovascular death, non-fatal MI or non-fatal stroke. In some embodiments MACE is cardiovascular death. In some embodiments MACE is non-fatal MI. In some embodiments MACE is non-fatal stroke. The term "non-fatal MI" as used herein refers to non-fatal myocardial infarction. In some embodiments MACE is events selected from the group consisting of cardiovascular death, non-fatal MI, and non-fatal stroke. In some embodiments MACE is coronary revascularisation. In some embodiments MACE is hospitalisation for unstable angina pectoris. In some embodiments MACE is hospitalisation for chronic heart failure.

In some embodiments the present invention relates to the treatment of a subject having one or more vascular disease selected from the group consisting of cardiovascular disease, cerebrovascular disease, peripheral vascular disease, chronic renal failure, and chronic heart failure.

In some embodiments the present invention relates to the treatment of a subject having one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9.

In some embodiments the present invention relates to the treatment of a subject having
- Type 2 diabetes, and
- $HbA_{1c} \geq 7.0\%$
- or
- $HbA_{1c} < 7.0\%$ and current insulin treatment corresponding to ≥20 units/day of basal insulin, and
- ongoing treatment with one or more oral or injectable antidiabetic agent(s), and
- Age ≥50 years at screening and at least one of the below conditions:
  - prior myocardial infarction
  - prior stroke or prior transient ischaemic attack (TIA)
  - prior coronary, carotid or peripheral arterial revascularisation
  - >50% stenosis on angiography or other imaging of coronary, carotid or lower extremity arteries
  - history of symptomatic coronary heart disease documented by positive exercise stress test or any cardiac imaging, or unstable angina pectoris with ECG changes
  - asymptomatic cardiac ischemia documented by positive nuclear imaging test or exercise test or dobutamine stress echo
  - chronic heart failure NYHA class II-III
  - chronic kidney disease corresponding to glomerular filtration rate 30-59 mL/min/1.73 m$^2$ per CKD-EPI
- or
- Age ≥60 years at screening and at least one of the below risk factors:
  - microalbuminuria or proteinuria
  - hypertension and left ventricular hypertrophy by ECG or imaging
  - left ventricular systolic and diastolic dysfunction by imaging
  - ankle/brachial index <0.9.

In some embodiments the present invention relates to the treatment of a subject having type 2 diabetes. In some embodiments the present invention relates to the treatment of a subject having type 1 diabetes.

In some embodiments the method reduces or delays a major adverse cardiovascular event (MACE). In some embodiments the method reduces the risk of said subject developing a major adverse cardiovascular event (MACE). In some embodiments the method reduces the risk of said subject developing its first MACE. The term "first MACE" as used herein refers to the first MACE event of a subject after initiation of insulin degludec administration.

In some embodiments the one or more risk factors of vascular disease are selected from the group consisting of a) microalbuminuria or proteinuria; b) hypertension and/or left ventricular hypertrophy by ECG or imaging; c) left ventricular systolic or diastolic dysfunction by imaging; and d) ankle/brachial index <0.9. In some embodiments the risk factor of vascular disease is microalbuminuria. In some embodiments the risk factor of vascular disease is proteinuria. In some embodiments the risk factor of vascular disease is hypertension and left ventricular hypertrophy. In some embodiments the risk factor of vascular disease is left ventricular systolic dysfunction. In some embodiments the risk factor of vascular disease is left ventricular diastolic dysfunction. In some embodiments the risk factor of vascular disease is ankle/brachial index <0.9.

In some embodiments MACE is selected from the group consisting of CV death, non-fatal MI, non-fatal stroke, coronary revascularisation, hospitalisation for heart failure, and hospitalisation for unstable angina pectoris.

In some embodiments MACE is selected from the group consisting of CV death, non-fatal MI, non-fatal stroke, coronary revascularisation, and hospitalisation for heart failure. In some embodiments MACE is selected from the group consisting of CV death, non-fatal MI, and non-fatal stroke. In some embodiments MACE is cardiovascular death. In some embodiments MACE is non-fatal MI. In some embodiments MACE is non-fatal stroke. In some embodiments MACE is reduced or delayed by at least 10% compared to placebo. In some embodiments MACE is reduced or delayed by from about 5% to about 15% compared to placebo. In some embodiments MACE is reduced or delayed by from about 5% to about 10% compared to placebo. In some embodiments MACE is selected from cardiovascular death, non-fatal MI, and non-fatal stroke, and wherein said MACE is reduced by at least 10% compared to placebo, at least 20% compared to placebo or at least 30% compared to placebo.

In some embodiments said MACE has a hazard ratio of about 0.91 compared to placebo. In some embodiments said MACE has a hazard ratio of about 0.91 with a 95% confidence interval of (0.78; 1.06) compared to placebo.

In some embodiments said insulin degludec is administered as a chronic treatment for at least 12 months. In some embodiments said insulin degludec is administered as a chronic treatment for at least 15 months. In some embodiments said insulin degludec is administered as a chronic treatment for at least 18 months. In some embodiments said insulin degludec is administered as a chronic treatment for at least 21 months. In some embodiments said insulin degludec is administered as a chronic treatment for at least 24 months. In some embodiments said insulin degludec is administered as a chronic treatment for at least 30 months. In some embodiments said insulin degludec is administered as a chronic treatment for at least 36 months.

In some embodiments said cardiovascular disease or said risk of cardiovascular disease were present before the initiation of administration of insulin degludec.

In some embodiments the risk of said subject developing a MACE is reduced by at least 10% compared to placebo. In some embodiments the risk of said subject developing a MACE is reduced by from about 10% to about 15% compared to placebo. In some embodiments the subject developing its first MACE is reduced or delayed by at least 10% compared to placebo. In some embodiments the MACE is reduced or delayed by from about 10% to about 15% compared to placebo.

In some embodiments the method further reduces the risk of death of said subject, wherein the cause of said death is any cause. In some embodiments the risk of death of said subject is reduced by at least 10% compared to placebo. In some embodiments the risk of death of said subject is reduced by from about 10% to about 20% compared to placebo. In some embodiments the risk of death of said subject is reduced about 15% compared to placebo.

In some embodiments said subject is a female, has substantially Asian origin, and/or has substantially African origin.

In some embodiments said subject is a female. In some embodiments said subject is a female wherein said MACE is reduced by at least 20% compared to placebo. In some embodiments said subject is a female wherein said MACE has a hazard ratio of about 0.76 compared to placebo. In some embodiments said subject is a female wherein said MACE has a hazard ratio of about 0.76 with a 95% confidence interval of (0.59; 0.99) compared to placebo.

In some embodiments said subject has substantially Asian origin. In some embodiments said subject has substantially Asian origin wherein said MACE is reduced by at least 50% compared to placebo. In some embodiments said subject has substantially asian origin wherein said MACE has a hazard ratio of about 0.42 compared to placebo. In some embodiments said subject has substantially Asian origin wherein said MACE has a hazard ratio of about 0.42 with a 95% confidence interval of (0.22; 0.81) compared to placebo. The term "substantially Asian origin" means a subject which has mainly Asian origin as commonly understood. This may be determined e.g. by family background, genetic assessments and residence over time. In some embodiments a subject who has substantially Asian origin has residence in Asia. In some embodiments the term "residence" of a subject as used herein refers to the jurisdiction in which said subject has its address registered with the authorities of said jurisdiction, e.g. a country in Asia. In some embodiments a subject who has substantially Asian origin has a genetic profile typical for people having lived in Asia for many generations. In some embodiments a subject who has substantially Asian origin is of Asian origin. In some embodiments a subject who has substantially Asian origin has two parent who have both been born in Asia. In some embodiments a subject who has substantially Asian origin was born in Asia.

In some embodiments said subject has substantially African origin. In some embodiments said subject has substantially African origin wherein said MACE is reduced by at least 60% compared to placebo. In some embodiments said subject has substantially African origin wherein said MACE has a hazard ratio of about 0.30 compared to placebo. In some embodiments said subject has substantially African origin wherein said MACE has a hazard ratio of about 0.30 with a 95% confidence interval of (0.12; 0.77) compared to placebo. The term "substantially African origin" means a subject which has mainly African origin as commonly understood. This may be determined e.g. by family background, genetic assessments and residence over time. In some embodiments a subject who has substantially African origin has residence in Africa. In some embodiments a subject who has substantially African origin has a genetic profile typical for people having lived in Africa for many generations. In some embodiments a subject who has substantially African origin is of Asian origin. In some embodiments a subject who has substantially African origin has two parent who have both been born in Africa. In some embodiments a subject who has substantially African origin was born in Africa.

In some embodiments the subject has a BMI of at least 30 kg/m2. In some embodiments the subject has a BMI of from 30 to 50 mg/m2. In some embodiments the subject has a HbA1c of at least 7%, such as at least 7.5%, or at least 8.0%. In some embodiments the subject has a HbA1c of at least 7.0% or has a HbA1c less than 7.0% combined with being subject to insulin treatment corresponding to at least 20 units/day of basal insulin.

The term "basal insulins" as used herein is intended to mean insulins which have a protracted mode of action, i.e. the time of action is substantially longer than that of human insulin. Non-limiting examples of basal insulins may be found e.g. in WO 2005/012347. Commercially available basal insulins include insulin detemir, insulin glargine and insulin degludec.

In some embodiments the subject is diagnosed with type 2 diabetes within a period of no more than 10 years prior to initiation of administration of insulin degludec. In some embodiments the subject is at least 50 years of age and has a CV disease. In some embodiments the subject is at least 60 years of age and has a CV disease. In some embodiments the subject does not have chronic heart failure. In some embodiments the subject receives concomitant medication consisting of one oral antidiabetic drug (OAD). In some embodiments the subject has not previously received antidiabetic therapy. In some embodiments the subject does not receive additional antidiabetic therapy. In some embodiments the subject already receives treatment with one or more injectable antidiabetic agent(s). In some embodiments said one or more injectable antidiabetic agent(s) comprises insulin glargine.

In some embodiments the subject has moderate and/or severe renal impairment. In some embodiments the subject has moderate renal impairment. In some embodiments the subject has an eGFR of less than 60 mL/min/1.73 m$^2$, such as less than 40 mL/min/1.73 m$^2$ or less than 30 mL/min/1.73 m$^2$, wherein said eGFR may be determined by MDRD. In some embodiments the subject has an eGFR in the range of 30-59 mL/min/1.73 m$^2$, wherein said eGFR may be determined by MDRD. In some embodiments the subject has an eGFR in the range of more than 40 to less than 50 mL/min/1.73 m$^2$, wherein said eGFR may be determined by MDRD.

In some embodiments said insulin degludec is administered once daily. In some embodiments said administration of insulin degludec is a chronic treatment in which insulin degludec is administered for at least 9 months and wherein said method reduces or delays cardiovascular death, non-fatal myocardial infarction (MI) or non-fatal stroke. In some embodiments said administration of insulin degludec is a chronic treatment in which insulin degludec is administered for at least 12 months and wherein said method reduces or delays cardiovascular death, non-fatal myocardial infarction (MI) or non-fatal stroke. In some said administration of insulin degludec is a chronic treatment in which insulin degludec is administered for at least 15 months and wherein said method reduces or delays cardiovascular death, non-fatal myocardial infarction (MI) or non-fatal stroke. In some said administration of insulin degludec is a chronic treatment in which insulin degludec is administered for at least 18 months and wherein said method reduces or delays cardiovascular death, non-fatal myocardial infarction (MI) or non-fatal stroke. In some said administration of insulin degludec is a chronic treatment in which insulin degludec is administered for at least 21 months and wherein said method reduces or delays cardiovascular death, non-fatal myocardial infarction (MI) or non-fatal stroke. In some said administration of insulin degludec is a chronic treatment in which insulin degludec is administered for at least 24 months and wherein said method reduces or delays cardiovascular death, non-fatal myocardial infarction (MI) or non-fatal stroke. In some embodiments said administration of insulin degludec is a chronic treatment in which insulin degludec is administered for at least 27 months and wherein said method reduces or delays cardiovascular death, non-fatal myocardial infarction (MI) or non-fatal stroke. In some said administration of insulin degludec is a chronic treatment in which insulin degludec is administered for at least 30 months and wherein said method reduces or delays cardiovascular death, non-fatal myocardial infarction (MI) or non-fatal stroke. In some embodiments said administration of insulin degludec is a chronic treatment in which insulin degludec is administered for at least 33 months and wherein said method reduces or delays cardiovascular death, non-fatal myocardial infarction (MI) or non-fatal stroke. In some embodiments said administration of insulin degludec is a chronic treatment in which insulin degludec is administered for at least 36 months and wherein said method reduces or delays cardiovascular death, non-fatal myocardial infarction (MI) or non-fatal stroke. In some embodiments said administration of insulin degludec is a chronic treatment in which insulin degludec is administered for at least 42 months and wherein said method reduces or delays cardiovascular death, non-fatal myocardial infarction (MI) or non-fatal stroke.

In some embodiments the terms "cardiovascular death" or "CV death" are used interchangeably herein to describe death, wherein the cause of death is selected from the group consisting of cardiovascular disease or is unknown. In some embodiments CV death is selected from the group consisting of death from cardiovascular causes, and deaths for which there was no clearly documented non-vascular cause. Death from cardiovascular causes may include sudden cardiac death, death due to acute myocardial infarction, death due to heart failure, and death due to stroke.

In some embodiments the terms "cardiovascular death" or "CV death" are used interchangeably herein to describe death, wherein the cause of death is selected from the group consisting of cardiovascular disease, also referred to herein as "CV death excluding death from unknown cause".

In some embodiments non-fatal MI is myocardial necrosis consistent with myocardial ischemia without death of the subject. In some embodiments MI is diagnosed based on the redefinitions suggested by the ESC (European Society of Cardiology)/ACCF (American College of Cardiology Foundation)/AHA (American Heart Association)/WHF (World Heart Federation) task force, as described in Thygesen K, et al. "Universal Definition of Myocardial Infarction." J Am Coll Cardiol 2007 Nov. 27; 50 (22): 2173-95.

In some embodiments coronary revascularisation is restoration of blood circulation in the heart, such as achieved by unblocking obstructed or disrupted blood vessels, or by surgically implanting replacements.

In some embodiments hospitalisation for unstable angina pectoris (UAP) is unplanned hospitalisation caused by ischemic symptoms suggestive of acute coronary syndrome and no elevation in cardiac biomarkers, including no elevation of troponin and cardiac biomarkers are negative for myocardial necrosis. Elevation of troponin may be at least 1 value above the 99th percentile of the upper reference limit, e.g. determined as Cardiac troponin I or Cardiac troponin T. Elevation of troponin may be Cardiac troponin I (cTnI) (e.g. determined by TnI-Ultra assay on the ADVIA Centaur XP immunoanalyzer, both Siemens Healthcare Diagnostics) of more than 0.04 ng/mL. In some embodiments UAP is not present when STEMI or NSTEMI are present (Criteria for STEMI: New ST segment elevation is present in 2 or more contiguous leads on the 12-lead ECG; Criteria for NSTEMI: ST segment elevation is absent in 2 or more contiguous leads on the 12-lead ECG; wherein said ECG shows manifestations of acute myocardial ischemia and may involve 1) ST elevation New ST elevation at the J-point in two contiguous leads with the cutoff points: ≥0.2 mV in men or ≥0.15 mV in women in leads V2-V3 and/or ≥0.1 mV in other leads; and/or 2) ST depression and T-wave changes New horizontal or down-sloping ST depression≥0.05 mV in two contiguous leads; and/or T inversion≥0.1 mV in two contiguous leads with prominent R-wave or R/S ratio>1). Acute coronary syndrome may involve at least one criteria selected from the group consisting of: New or worsening ST or T wave changes on ECG, wherein said ECG changes satisfy at least one of the following criteria for acute myocardial ischemia (in the absence of left ventricular hypertrophy and left bundle branch block): ST elevation; New transient (known to be <20 minutes) ST elevation at the J-point in two contiguous leads with the cut-off points: ≥0.2 mV in men or ≥0.15 mV in women in leads V2-V3 and/or ≥0.1 mV in other leads, ST depression and T-wave changes, New horizontal or down-sloping ST depression≥0.05 mV in two contiguous leads; and/or T inversion≥0.1 mV in two contiguous leads with prominent Rwave or R/S ratio>1; Evidence of ischemia on stress testing with cardiac imaging; Evidence of ischemia on stress testing without cardiac imaging but with angiographic evidence of ≥70% lesion and/or thrombus in an epicardial coronary artery or initiation/increased dosing of antianginal therapy; and Angiographic evidence of ≥70% lesion and/or thrombus in an epicardial coronary artery In some embodiments non-fatal stroke is stroke without death of the subject, wherein stroke includes transient ischemic attack, ischemic stroke, and hemorrhagic stroke. In some embodiments transient ischemic attack (TIA) is defined as a transient episode of neurological dysfunction caused by focal brain, spinal cord, or retinal ischemia, without acute infarction. In some embodiments ischemic stroke is defined as an acute episode of focal cerebral, spinal, or retinal dysfunction caused by an infarction of central nervous system tissue that results from a thrombus or embolus impairing central nervous system perfusion (not due to hemorrhage) and is documented by imaging; in addition, evidence of ischemic stroke obtained from autopsy can also confirm the diagnosis, and/or findings on lumbar puncture can be supportive to the diagnosis. In some embodiments hemorrhagic stroke is defined as an acute episode of focal or global cerebral, spinal, or retinal dysfunction caused by a nontraumatic intraparenchymal, intraventricular, or subarachnoid hemorrhage with documentation of cerebral hemorrhage on imaging (e.g., CT or MRI scan), i.e. intraparenchymal, intraparenchymal with penetration into the ventricles, intraventricular, or subarachnoidal hemorrhage; subdural and epidural bleedings are not included; in addition, evidence of hemorrhagic stroke obtained from autopsy can also confirm the diagnosis, and/or findings on lumbar puncture can be supportive to the diagnosis.

In some embodiments hospitalisation for heart failure is hospitalization defined as an admission to an inpatient unit or a visit to an emergency department that results in at least a 12 hour stay, wherein at least one of the following clinical manifestations of heart failure is present: New or worsening dyspnea, new or worsening orthopnea, new or worsening paroxysmal nocturnal dyspnea, new or worsening edema, new or worsening pulmonary basilar crackles, new or worsening jugular venous distension, new or worsening third heart sound or gallop rhythm, or radiological evidence of worsening heart failure. Hospitalisation for heart failure may also involve (i) additional and/or increased therapy, including a) initiation of intravenous diuretic, inotrope, or vasodilator therapy; b) uptitration of intravenous therapy, if already on therapy; c) initiation of mechanical or surgical intervention (mechanical circulatory support; d) heart transplantation or ventricular pacing to improve cardiac function), or the use of ultrafiltration, hemofiltration, or dialysis that is specifically directed at treatment of heart failure; and/or (ii) biomarker results (e.g., brain natriuretic peptide) consistent with congestive heart failure will be supportive of this diagnosis.

In some embodiments the methods of the present invention reduce the occurrence of an event. In some embodiments "reduces or delays" when used herein with reference to the method of the invention is "reduces the risk of".

Subject and Subpopulations

The subject to be administered insulin degludec according to the present invention may be human, such as an adult human. The subject to receive insulin degludec administration according to the methods of the present invention may have type 2 diabetes and has (i) one or more vascular diseases selected from the group consisting of cardiovascular disease, cerebrovascular disease, peripheral vascular disease, chronic renal failure, and/or chronic heart failure, and/or (ii) one or more risk factors of vascular disease. In some embodiments the subject has type 2 diabetes and cardiovascular disease, cerebrovascular disease, peripheral vascular disease, chronic renal failure, and/or chronic heart failure. The subject may have type 2 diabetes and cardiovascular disease. The subject may have type 2 diabetes and cerebrovascular disease. The subject may have type 2 diabetes and peripheral vascular disease. The subject may have type 2 diabetes and chronic renal failure. The subject may have type 2 diabetes and chronic heart failure. In some embodiments the subject has type 2 diabetes and one or more risk factors of vascular disease. These vascular diseases may be referred to as concomitant, i.e. one or more vascular diseases are present in the subject at the same time as type 2 diabetes.

In some embodiments the subject is at least 50 years of age, such as at least 60 years of age.

In some embodiments the subject has $HbA_{1c}$ of at least 7.0%, e.g. prior to receiving insulin degludec administration. In some embodiments the subject has $HbA_{1c}$ of more than 8.3%, e.g. prior to receiving insulin degludec administration. In some embodiments the subject has $HbA_{1c}$ of at least 8.4%, e.g. prior to receiving insulin degludec administration. In some embodiments the subject has $HbA_{1c}$ of at least 9.0%, e.g. prior to receiving insulin degludec administration. $HbA_{1c}$ may be determined according to methods known in the art, for example as a percentage determined according to the method defined by the Diabetes Control and Complications Trial (DCCT), see New Engl J Med 1993; 329:977-986.

In some embodiments the subject is, except for insulin degludec, anti-diabetic drug naive or treated with one or more oral anti-diabetic drugs (OADs) or treated with human NPH insulin or long-acting insulin analogue or premixed insulin, alone or in combination with OAD(s). The subject may be anti-diabetic drug naive. The subject may be treated with one or more oral anti-diabetic drugs (OADs). The subject may be treated with human NPH insulin or long-acting insulin analogue or premixed insulin, alone or in combination with OAD(s). In some embodiments the OAD may be selected from the group consisting of sulfonylureas, insulin secretagogues, thiazolidinediones, alpha-glucosidase inhibitors, dipeptidyl peptidase-4 inhibitors, sodium-glucose co-transporter-2 inhibitors, and combinations thereof. In some embodiments the OAD is sulfonylurea (e.g. glimepiride, glipizide, glyburide). In some embodiments the OAD is insulin secretagogues (e.g. biguanides such as metformin or meglitinides such as nateglinide). In some embodiments the OAD is thiazolidinediones (e.g. pioglitazone, rosiglitazone). In some embodiments the OAD is alpha-glucosidase inhibitors (e.g. acarbose, miglitol, voglibose). In some embodiments the OAD is sodium-glucose co-transporter-2 inhibitors (e.g. dapagliflozin, canagliflozin, empagliflozin). In some embodiments the OAD is dipeptidyl peptidase-4 inhibitors (e.g. sitagliptin). In some embodiments the OAD is not a dipeptidyl peptidase-4 inhibitor.

In some embodiments the subject (i) is at least 50 years of age and has cardiovascular disease, cerebrovascular disease, peripheral vascular disease, chronic renal failure, and/or chronic heart failure, or (ii) is at least 60 years of age and has one or more risk factors of vascular disease. In some embodiments the subject is at least 60 years of age and has cardiovascular disease, cerebrovascular disease, peripheral vascular disease, chronic renal failure, and/or chronic heart failure. In some embodiments the subject is at least 60 years of age and has cardiovascular disease, cerebrovascular disease, peripheral vascular disease, chronic renal failure, and/ or chronic heart failure.

In some embodiments the subject a) (i) is at least 50 years of age and has one or more vascular diseases selected from the group consisting of cardiovascular disease, cerebrovascular disease, peripheral vascular disease, chronic renal failure, and/or chronic heart failure, or (ii) is at least 60 years of age and has risk factors of vascular disease; b) has $HbA_{1c}$ of at least 7.0%, e.g. at the time prior to receiving insulin degludec administration; and c) is anti-diabetic drug naive or treated with one or more oral anti-diabetic drugs (OADs) or treated with human NPH insulin or long-acting insulin analogue or premixed insulin, alone or in combination with OAD(s).

In some embodiments the subject has renal impairment. In some embodiments the subject has moderate renal impairment (i.e. eGFR 30-59 per MDRD). In some embodiments the subject has severe renal impairment (i.e. eGFR <30 per MDRD). In some embodiments the subject has renal impairment, wherein the estimated glomerular filtration rate (eGFR) is <60, for example <60 mL/min/1.73 m² per Modification of Diet in Renal Disease (MDRD). In some embodiments the subject has eGFR of <60 mL/min/1.73 m² per MDRD. In some embodiments the subject has eGFR of <50 mL/min/1.73 m² per MDRD. In some embodiments the subject has eGFR of <40 mL/min/1.73 m² per MDRD. In some embodiments the subject has eGFR of <30 mL/min/ 1.73 m² per MDRD. In some embodiments the subject has eGFR of ≥10 mL/min/1.73 m² per MDRD. In some embodiments the estimated glomerular filtration rate (eGFR) is calculated based on serum creatinine concentration followed by either the equation Modification of Diet in Renal Disease (MDRD) or the Chronic Kidney Disease Epidemiology Collaboration (CKD-EPI), both involving variables for age, gender, and race of the subject. eGFR determined by MDRD may be referred to as eGFR-MDRD. eGFR determined by CKD-EPI may be referred to as eGFR-CKD-EPI. The eGFR-MDRD equation may be as defined in formula V:
$$eGFR\ (mL/min/1.73\ m^2) = 175 \times (S_{cr})^{-1.154} \times (Age)^{-0.203} \times (0.742\ if\ female) \times (1.212\ if\ African\ American)\ [V].$$
The CKD-EPI equation may be as defined in formula VI:
$$eGFR = 141 \times min^{\alpha} \times max^{-1.209} \times 0.993^{Age} \times (1.018\ if\ female) \times (1.159\ if\ black)\ [VI],$$
wherein "min" indicates the minimum of $S_{cr}/\kappa$ or 1, "max" indicates the maximum of $S_{cr}/\kappa$ or 1, $S_{cr}$ is serum creatinine in mg/dL, κ is 0.7 for females and 0.9 for males, and α is −0.329 for females or −0.411 for males.

In some embodiments the cardiovascular disease, cerebrovascular disease, peripheral vascular disease, chronic renal failure, and/or chronic heart failure are selected from the group consisting of myocardial infarction, stroke, transient ischaemic attack (TIA), coronary revascularisation, carotid revascularisation, peripheral arterial revascularisation, >50% stenosis of coronary arteries, >50% stenosis of carotid arteries, >50% stenosis of lower extremity arteries, history of symptomatic coronary heart disease (e.g. documented by positive exercise stress test or any cardiac imaging), unstable angina pectoris (e.g. with ECG (electrocardiogram) changes), asymptomatic cardiac ischemia (e.g. documented by positive nuclear imaging test or exercise test or dobutamine stress echo), chronic heart failure NYHA class II-III, and moderate-severe chronic renal failure (e.g. having clinically reached a stage corresponding to a glomerular filtration rate<60 mL/min/1.73 m² per Modification of Diet in Renal Disease (MDRD) or <60 mL/min per Cockroft-Gault formula). In some embodiments the cardiovascular disease, cerebrovascular disease, peripheral vascular disease, chronic renal failure, and/or chronic heart failure is selected from the group consisting of myocardial infarction, stroke, transient ischaemic attack (TIA), coronary revascularisation, carotid revascularisation, peripheral arterial revascularisation, wherein the event occurred before initiating insulin degludec administration. In some embodiments the cardiovascular disease, cerebrovascular disease, peripheral vascular disease, chronic renal failure, and/or chronic heart failure may be selected from the group consisting of: a) myocardial infarction; b) stroke or prior transient ischaemic attack (TIA); c) coronary revascularisation, carotid revascularisation, or peripheral arterial revascularisation; d) >50% stenosis on angiography or other imaging of coronary, carotid or lower extremity arteries; e) history of symptomatic coronary heart disease documented by positive exercise stress test or any cardiac imaging, or unstable angina pectoris with ECG (electrocardiogram) changes; f) asymptomatic cardiac ischemia documented by positive nuclear imaging test or exercise test or dobutamine stress echo; g) chronic heart failure NYHA class II-III; and h) chronic renal failure, having clinically reached a stage corresponding to a glomerular filtration rate<60 mL/min/1.73 m² per Modification of Diet in Renal Disease (MDRD) or <60 mL/min per Cockroft-Gault formula. In some embodiments, the subject experienced the a) myocardial infarction; b) stroke or transient ischaemic attack (TIA); or c) coronary, carotid or peripheral arterial revascularisation as a prior event before the time of insulin degludec administration. In some embodiments the cardiovascular disease, cerebrovascular disease, peripheral vascular disease, chronic renal failure, and/or chronic heart failure is selected from the group consisting of prior myocardial infarction, prior stroke, and prior transient ischaemic attack (TIA). In some embodiments the cardiovascular disease, cerebrovascular disease, peripheral vascular disease, chronic renal failure, and/or chronic heart failure is selected from the group consisting of prior coronary revascularisation, prior carotid revascularisation, and prior peripheral arterial revascularisation. In some embodiments the cardiovascular disease, cerebrovascular disease, peripheral vascular disease, chronic renal failure, and/or chronic heart failure is selected from the group consisting of >50% stenosis of coronary arteries, >50% stenosis of carotid arteries, and >50% stenosis of lower extremity arteries. In some embodiments the cardiovascular disease, cerebrovascular disease, peripheral vascular disease, chronic renal failure, and/or chronic heart failure is selected from the group consisting of history of symptomatic coronary heart disease (e.g. documented by positive exercise stress test or any cardiac imaging), and unstable angina pectoris (e.g. with ECG (electrocardiogram) changes). In some embodiments the cardiovascular disease, cerebrovascular disease, peripheral vascular disease, chronic renal failure, and/or chronic heart failure is selected from the group consisting of asymptomatic cardiac ischemia (e.g. documented by positive nuclear imaging test or exercise test or dobutamine stress echo). In some embodiments the cardiovascular disease, cerebrovascular disease, peripheral vascular disease, chronic renal failure, and/or chronic heart failure is selected from the group consisting of chronic heart failure NYHA class II-III. In some embodiments the cardiovascular disease, cerebrovascular disease, peripheral vascular disease, chronic renal failure, and/or chronic heart failure is selected from the group consisting of moderate-severe chronic renal failure (e.g. having clinically reached a stage corresponding to a glomerular filtration rate<60 mL/min/1.73 m² per Modification of Diet in Renal Disease (MDRD) or <60 mL/min per Cockroft-Gault formula). In some embodiments the "prior" as used herein refers to before insulin degludec administration.

The glomerular filtration rate may alternatively be determined by the "Cockroft-Gault formula" may be as defined by Formula III: CrCl (mL/min)=(N×[140-age (years)]×weight* (kg))/Serum creatinine (μM) [III], wherein CrCl is the Cockcroft and Gault creatinine clearance, wherein N is 1.23 for males and 1.04 for females, and wherein if actual weight is greater than 120% IBW then weight is the ideal body weight (IBW) as defined in Formula IIIa: IBW (kg)= (no of inches over 5 ft×2.3)+M [IIIa], wherein M is 50 for males and 45.5 for females.

Heart failure exists in different degrees of severity. The most commonly used classification system of heart failure is the New York Heart Association Functional Classification (also referred to as "NYHA"). NYHA categorises subjects in one of four classes I-IV (Table A), based on their degree of limitation during physical activity, and optionally an additional subgroup A-D based on objective assessments, for further details see The Criteria Committee of the New York Heart Association. Nomenclature and Criteria for Diagnosis of Diseases of the Heart and Great Vessels. 9th ed. Boston, Mass.: Little, Brown & Co; 1994:253-256). In some embodiments the subject has heart failure NYHA class I-III, such as class I, class II or class III.

TABLE A

NYHA class I-IV criteria

| NYHA Class | Functional Capacity of the subject |
|---|---|
| I | Subjects with cardiac disease but without resulting limitation of physical activity. Ordinary physical activity does not cause undue fatigue, palpitation, dyspnea, or anginal pain. |
| II | Subjects with cardiac disease resulting in slight limitation of physical activity. They are comfortable at rest. Ordinary physical activity results in fatigue, palpitation, dyspnea, or anginal pain. |
| III | Subjects with cardiac disease resulting in marked limitation of physical activity. They are comfortable at rest. Less than ordinary activity causes fatigue, palpitation, dyspnea, or anginal pain. |

TABLE A-continued

NYHA class I-IV criteria

| NYHA Class | Functional Capacity of the subject |
|---|---|
| IV | Subjects with cardiac disease resulting in inability to carry on any physical activity without discomfort. Symptoms of heart failure or the anginal syndrome may be present even at rest. If any physical activity is undertaken, discomfort is increased. |

The "cardiovascular disease, cerebrovascular disease, peripheral vascular disease, chronic renal failure, and/or chronic heart failure" may be myocardial infarction. The "cardiovascular disease, cerebrovascular disease, peripheral vascular disease, chronic renal failure, and/or chronic heart failure" may be stroke or prior transient ischaemic attack (TIA). The "cardiovascular disease, cerebrovascular disease, peripheral vascular disease, chronic renal failure, and/or chronic heart failure" may be coronary, carotid or peripheral arterial revascularisation. The "cardiovascular disease, cerebrovascular disease, peripheral vascular disease, chronic renal failure, and/or chronic heart failure" may be >50% stenosis on angiography or other imaging of coronary, carotid or lower extremity arteries. The "cardiovascular disease, cerebrovascular disease, peripheral vascular disease, chronic renal failure, and/or chronic heart failure" may be history of symptomatic coronary heart disease documented by positive exercise stress test or any cardiac imaging, or unstable angina pectoris with ECG changes. The "cardiovascular disease, cerebrovascular disease, peripheral vascular disease, chronic renal failure, and/or chronic heart failure" may be asymptomatic cardiac ischemia documented by positive nuclear imaging test or exercise test or dobutamine stress echo. The "cardiovascular disease, cerebrovascular disease, peripheral vascular disease, chronic renal failure, and/or chronic heart failure" may be chronic heart failure NYHA class II-III. The "cardiovascular disease, cerebrovascular disease, peripheral vascular disease, chronic renal failure, and/or chronic heart failure" may be chronic renal failure, having clinically reached a stage corresponding to a glomerular filtration rate<60 mL/min/1.73 m$^2$ per Modification of Diet in Renal Disease (MDRD) or <60 mL/min per Cockroft-Gault formula.

In some embodiments the subject has a BMI of at least 30 kg/m$^2$. BMI (body mass index) is a measure of body fat based on height and weight. The formula for calculation is BMI=(weight in kilograms)/(height in meters)$^2$. In some embodiments the subject has a BMI in the range of 30-50 kg/m$^2$. In some embodiments the subject has a BMI of at least 33 kg/m$^2$. In some embodiments the subject has a BMI of at least 35 kg/m$^2$. In some embodiments the subject has a BMI of at least 37 kg/m$^2$. In some embodiments the subject has a BMI of at least 40 kg/m$^2$. In some embodiments the subject has a BMI of up to 45 kg/m$^2$. In some embodiments the subject has a BMI of up to 40 kg/m$^2$.

In some embodiments the subject does not have type 1 diabetes. In some embodiments the subject already receives administration of a basal insulin prior to initiating administration of insulin degludec according to the present invention. In some embodiments the subject already receives administration of a basal insulin which is not insulin degludec prior to initiating administration of insulin degludec according to the present invention. In some embodiments the subject does not have an acute coronary or cerebrovascular event in the previous 14 days. In some embodiments the subject does not receive continuous renal replacement therapy. In some embodiments the subject does not have end-stage liver disease. In some embodiments the subject does not have chronic heart failure NYHA IV. In some embodiments the subject does not have a prior solid organ transplant or awaiting solid organ transplant.

Insulin Degludec

Insulin degludec is the compound $N^{\varepsilon B29}$—($N^{\alpha}$—(HOOC$(CH_2)_{14}$CO)-γ-Glu) desB30 human insulin. Insulin degludec may be prepared as described in WO2005/012347.

Pharmaceutical Composition

Insulin degludec may be administered in the form of a pharmaceutical composition. The pharmaceutical composition may comprise insulin degludec in a concentration from 300 to 1800 nmol/mL. In some embodiments the pharmaceutical composition comprises 300-1800 nmol/mL, 500-1300 nmol/mL, about 600 nmol/mL, or about 1200 nmol/mL insulin degludec. In some embodiments the pharmaceutical composition comprises 600-1200 nmol/mL insulin degludec.

The pharmaceutical compositions described herein may further comprise one or more pharmaceutically acceptable excipients, for example selected from the group consisting of buffer system, preservative, tonicity agent, chelating agent, stabilizer and surfactant. In some embodiments the pharmaceutical composition comprises one or more pharmaceutically acceptable excipients, such as one or more selected from the group consisting of a buffer, an isotonic agent, and a preservative. The formulation of pharmaceutically active ingredients with various excipients is known in the art, see e.g. Remington: The Science and Practice of Pharmacy (e.g. 19th edition (1995), and any later editions). The term "excipient" broadly refers to any component other than the active therapeutic ingredient(s), e.g. insulin degludec. The excipient may be an inert substance, an inactive substance, and/or a not medicinally active substance.

In some embodiments the pharmaceutical composition comprises a phosphate buffer, such as a sodium phosphate buffer, e.g. disodium phosphate. In some embodiments the pharmaceutical composition comprises an isotonic agent, such as glycerol. In some embodiments the pharmaceutical composition comprises a preservative, such as phenol or a mixture of phenol and m-cresol.

The pharmaceutical composition may be in the form of a solution or a suspension. In some embodiments the pharmaceutical composition is aqueous composition, such as an aqueous solution or an aqueous suspension. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. An aqueous composition may comprise at least 50% w/w water, or at least 60%, 70%, 80%, or even at least 90% w/w of water. In some embodiments the pharmaceutical composition has a pH in the range of 7.0-8.0.

In some embodiments insulin degludec is administered in the form of a pharmaceutical composition comprising from about 600 to 1200 nmol/mL insulin degludec and from about 20 to about 80 μg/mL zinc. In some embodiments insulin degludec is administered in the form of a pharmaceutical composition comprising about 600 nmol/mL insulin degludec, about 1.50 mg/mL phenol, about 1.72 mg/mL metacresol, about 19.6 mg/mL glycerol, about 32.7 μg/mL zinc, and pH is about 7.6. In some embodiments insulin degludec is administered in the form of a pharmaceutical composition comprising 600 nmol/mL insulin degludec, 1.50 mg/mL phenol, 1.72 mg/mL metacresol, 19.6 mg/mL glycerol, 32.7

μg/mL zinc, and pH is 7.6. In some embodiments insulin degludec is administered in the form of a pharmaceutical composition comprising about 1200 nmol/mL insulin degludec, about 1.50 mg/mL phenol, about 1.72 mg/mL metacresol, about 19.6 mg/mL glycerol, about 71.9 μg/mL zinc, and pH is about 7.6. In some embodiments insulin degludec is administered in the form of a pharmaceutical composition comprising 1200 nmol/mL insulin degludec, 1.50 mg/mL phenol, 1.72 mg/mL metacresol, 19.6 mg/mL glycerol, 71.9 μg/mL zinc, and pH is 7.6.

In some embodiments insulin degludec is administered together with liraglutide, e.g. in the form of a combination formulation comprising insulin degludec and liraglutide. Liraglutide is the GLP-1 receptor agonist Arg34,Lys26-(N-epsilon-(gamma-L-glutamyl(N-alfa-hexadecanoyl)))-GLP-1(7-37). Liraglutide may be prepared as described in Example 37 of WO98/08871. In some embodiments insulin degludec is administered in the form of a pharmaceutical composition comprising about 600 nmol/mL insulin degludec, about 3.6 mg/mL liraglutide, about 5.70 mg/mL phenol, about 19.7 mg/mL glycerol, about 55 μg/mL zinc (as zinc acetate), and pH 8.15. In some embodiments insulin degludec is administered in the form of a pharmaceutical composition comprising 600 nmol/mL insulin degludec, 3.6 mg/mL liraglutide, 5.70 mg/mL phenol, 19.7 mg/mL glycerol, 55 μg/mL zinc (as zinc acetate), and pH 8.15.

Administration Regimen

Insulin degludec may be administered in a therapeutically effective amount, such as an amount therapeutically effective to treat type 2 diabetes. The therapeutically effective amount of insulin degludec can be assessed by a medical doctor. The dosage of insulin degludec may be in the range from 0 to 100 units (U), such as from 20 to 100 U.

Insulin degludec may be administered once daily. In some embodiments insulin degludec is administered once daily at any time in the day. In some embodiments the daily dosage of insulin degludec is in the range from 20 to 100 U, such as in the range from 40 to 80 U.

In some embodiments the term "chronic treatment" as used herein with reference to insulin degludec means administration in an amount and frequency to provide a therapeutic effect. In some embodiments the term "chronic treatment" as used herein with reference to insulin degludec means once daily administration 0-100 U, such as 20-100 U insulin degludec.

Insulin degludec may be administered via parenteral administration, for example subcutaneous injection. Insulin degludec may be administered using a pen-injector, such as a 3 ml disposable pen-injector.

Unless otherwise stated, ranges herein include their end points. In some embodiments the term "a" means "one or more". In some embodiments, and unless otherwise indicated in the specification, terms presented in singular form also include the plural situation. Herein the term "about" means±10% of the value referred to, and includes the value.

Non-Limiting Embodiments of the Invention

Non-limiting embodiments of the invention include:

1. A method for treating diabetes, comprising administration of a basal insulin in a therapeutically effective amount to a subject in need thereof, wherein said subject has a cardiovascular disease or is at risk of developing a cardiovascular disease and wherein said basal insulin is insulin degludec, and wherein said method delays or reduces major adverse cardiovascular event (MACE).

2. The method according to embodiment 1, wherein said subject is a female, has substantially Asian origin, and/or has substantially African origin.
3. The method according to embodiment 1, wherein said subject has
   (i) one or more vascular disease selected from the group consisting of cardiovascular disease, cerebrovascular disease, peripheral vascular disease, chronic renal failure, and chronic heart failure, and/or
   (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9.
4. The method according to any of the preceding embodiments, wherein said subject has one or more vascular disease selected from the group consisting of cardiovascular disease, cerebrovascular disease, peripheral vascular disease, chronic renal failure, and chronic heart failure.
5. The method according to any of the preceding embodiments, wherein said subject has one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9.
6. The method according to any of the preceding embodiments, wherein said subject has
   Type 2 diabetes, and
   $HbA_{1c} \geq 7.0\%$
   or
   $HbA_{1c} <7.0\%$ and current insulin treatment corresponding to ≥20 units/day of basal insulin, and
   ongoing treatment with one or more oral or injectable antidiabetic agent(s), and
   Age ≥50 years at screening and at least one of the below conditions:
   prior myocardial infarction
   prior stroke or prior transient ischaemic attack (TIA)
   prior coronary, carotid or peripheral arterial revascularisation
   >50% stenosis on angiography or other imaging of coronary, carotid or lower extremity arteries
   history of symptomatic coronary heart disease documented by positive exercise stress test or any cardiac imaging, or unstable angina pectoris with ECG changes
   asymptomatic cardiac ischemia documented by positive nuclear imaging test or exercise test or dobutamine stress echo
   chronic heart failure NYHA class II-III
   chronic kidney disease corresponding to glomerular filtration rate 30-59 mL/min/1.73 m$^2$ per CKD-EPI
   or
   Age ≥60 years at screening and at least one of the below risk factors:
   microalbuminuria or proteinuria
   hypertension and left ventricular hypertrophy by ECG or imaging
   left ventricular systolic and diastolic dysfunction by imaging
   ankle/brachial index <0.9.
7. The method according to any of the preceding embodiments, wherein said diabetes is type 2 diabetes.

8. The method according to any of embodiments 1-6, wherein said diabetes is type 1 diabetes.
9. The method according to any of the preceding embodiments, wherein said MACE is selected from cardiovascular death, non-fatal MI, non-fatal stroke, coronary revascularisation and hospitalisation for heart failure.
10. The method according to any of the preceding embodiments, wherein said MACE is selected from cardiovascular death, non-fatal MI, and non-fatal stroke.
11. The method according to any of the preceding embodiments, wherein said MACE is cardiovascular death.
12. The method according to any of embodiments 1-10, wherein said MACE is non-fatal MI.
13. The method according to any of embodiments 1-10, wherein said MACE is non-fatal stroke.
14. The method according to any of the preceding embodiments, wherein said MACE is selected from cardiovascular death, non-fatal MI, and non-fatal stroke, and wherein said MACE is reduced by at least 10% compared to placebo, at least 20% compared to placebo or at least 30% compared to placebo.
15. The method according to any of the preceding embodiments, wherein said MACE has a hazard ratio of about 0.91 compared to placebo.
16. The method according to any of the preceding embodiments, wherein said MACE has a hazard ratio of about 0.91 with a 95% confidence interval of (0.78; 1.06) compared to placebo.
17. The method according to any of the preceding embodiments, wherein insulin degludec is administered as a chronic treatment for at least 12 months.
18. The method according to any of the preceding embodiments, wherein insulin degludec is administered as a chronic treatment for at least 15 months.
19. The method according to any of the preceding embodiments, wherein insulin degludec is administered as a chronic treatment for at least 18 months.
20. The method according to any of the preceding embodiments, wherein insulin degludec is administered as a chronic treatment for at least 21 months.
21. The method according to any of the preceding embodiments, wherein insulin degludec is administered as a chronic treatment for at least 24 months.
22. The method according to any of the preceding embodiments, wherein insulin degludec is administered as a chronic treatment for at least 30 months.
23. The method according to any of the preceding embodiments, wherein insulin degludec is administered as a chronic treatment for at least 36 months.
24. The method according to any of the preceding embodiments, wherein said cardiovascular disease or said risk of cardiovascular disease were present before the initiation of administration of insulin degludec.
25. The method according to any of the preceding embodiments, wherein said subject is a female.
26. The method according to embodiment 25 wherein said MACE is reduced by at least 20% compared to placebo.
27. The method according to embodiment 25 wherein said MACE has a hazard ratio of about 0.76 compared to placebo.
28. The method according to any of embodiments 25-27, wherein said MACE has a hazard ratio of about 0.76 with a 95% confidence interval of (0.59; 0.99) compared to placebo.
29. The method according to any of the preceding embodiments, wherein said subject has substantially Asian origin.
30. The method according to embodiment 29 wherein said MACE is reduced by at least 50% compared to placebo.
31. The method according to embodiment 29 wherein said MACE has a hazard ratio of about 0.42 compared to placebo.
32. The method according to any of embodiments 29-31, wherein said MACE has a hazard ratio of about 0.42 with a 95% confidence interval of (0.22; 0.81) compared to placebo.
33. The method according to any of the preceding embodiments, wherein said subject has substantially African origin.
34. The method according to embodiment 33 wherein said MACE is reduced by at least 60% compared to placebo.
35. The method according to embodiment 33 wherein said MACE has a hazard ratio of about 0.30 compared to placebo.
36. The method according to any of embodiments 33-35, wherein said MACE has a hazard ratio of about 0.30 with a 95% confidence interval of (0.12; 0.77) compared to placebo.
37. The method according to any of the preceding embodiments, wherein said method delays MACE.
38. The method according to any of the preceding embodiments, wherein said subject has a BMI of at least 30 kg/m2.
39. The method according to any of the preceding embodiments, wherein said subject has a HbA1c of at least 7%, such as at least 7.5%, or at least 8.0%.
40. The method according to any of the preceding embodiments, wherein said subject has a HbA1c of at least 7.0% or has a HbA1c less than 7.0% combined with being subject to insulin treatment corresponding to at least 20 units/day of basal insulin.
41. The method according to any of the preceding embodiments, wherein said subject already receives treatment with one or more oral antidiabetic agent(s).
42. The method according to any of the preceding embodiments, wherein said subject already receives treatment with one or more injectable antidiabetic agent(s).
43. The method according to embodiment 42 wherein said one or more injectable antidiabetic agent(s) comprises insulin glargine.
44. The method according to any of the preceding embodiments, wherein said administration of insulin degludec is a chronic treatment in which insulin degludec is administered for at least 9 months and wherein said method reduces or delays cardiovascular death, non-fatal myocardial infarction (MI) or non-fatal stroke.
45. The method according to any of the preceding embodiments, wherein said administration of insulin degludec is a chronic treatment in which insulin degludec is administered for at least 12 months and wherein said method reduces or delays cardiovascular death, non-fatal myocardial infarction (MI) or non-fatal stroke.
46. The method according to any of the preceding embodiments, wherein said administration of insulin degludec is a chronic treatment in which insulin degludec is administered for at least 15 months and wherein said method reduces or delays cardiovascular death, non-fatal myocardial infarction (MI) or non-fatal stroke.

47. The method according to any of the preceding embodiments, wherein said administration of insulin degludec is a chronic treatment in which insulin degludec is administered for at least 18 months and wherein said method reduces or delays cardiovascular death, non-fatal myocardial infarction (MI) or non-fatal stroke.

48. The method according to any of the preceding embodiments, wherein said administration of insulin degludec is a chronic treatment in which insulin degludec is administered for at least 21 months and wherein said method reduces or delays cardiovascular death, non-fatal myocardial infarction (MI) or non-fatal stroke.

49. The method according to any of the preceding embodiments, wherein said administration of insulin degludec is a chronic treatment in which insulin degludec is administered for at least 24 months and wherein said method reduces or delays cardiovascular death, non-fatal myocardial infarction (MI) or non-fatal stroke.

50. The method according to any of the preceding embodiments, wherein said administration of insulin degludec is a chronic treatment in which insulin degludec is administered for at least 27 months and wherein said method reduces or delays cardiovascular death, non-fatal myocardial infarction (MI) or non-fatal stroke.

51. The method according to any of the preceding embodiments, wherein said administration of insulin degludec is a chronic treatment in which insulin degludec is administered for at least 30 months and wherein said method reduces or delays cardiovascular death, non-fatal myocardial infarction (MI) or non-fatal stroke.

52. The method according to any of the preceding embodiments, wherein said administration of insulin degludec is a chronic treatment in which insulin degludec is administered for at least 33 months and wherein said method reduces or delays cardiovascular death, non-fatal myocardial infarction (MI) or non-fatal stroke.

53. The method according to any of the preceding embodiments, wherein said administration of insulin degludec is a chronic treatment in which insulin degludec is administered for at least 36 months and wherein said method reduces or delays cardiovascular death, non-fatal myocardial infarction (MI) or non-fatal stroke.

54. The method according to any of the preceding embodiments, wherein said administration of insulin degludec is a chronic treatment in which insulin degludec is administered for at least 42 months and wherein said method reduces or delays cardiovascular death, non-fatal myocardial infarction (MI) or non-fatal stroke.

55. The method according to any of the preceding embodiments, wherein said subject is at least 50 years of age.

56. The method according to any of the preceding embodiments, wherein said subject is at least 60 years of age.

57. The method according to any of the preceding embodiments, wherein said subject has moderate and/or severe renal impairment.

58. The method according to any of the preceding embodiments, wherein said subject has moderate renal impairment.

59. The method according to any of the preceding embodiments, wherein said subject has an eGFR of less than 60 mL/min/1.73 m$^2$, such as less than 40 mL/min/1.73 m$^2$ or less than 30 mL/min/1.73 m$^2$, wherein said eGFR may be determined by MDRD.

60. The method according to any of the preceding embodiments, wherein said subject has an eGFR in the range of 30-59 mL/min/1.73 m$^2$, wherein said eGFR may be determined by MDRD.

61. The method according to any of the preceding embodiments, wherein said insulin degludec is administered once daily.

62. The method according to any of the preceding embodiments, wherein said insulin degludec is administered once daily in an amount in the range of 0-100 U per day, such as from 20-100 U per day.

63. The method according to any of the preceding embodiments, wherein said insulin degludec is administered once daily in an amount in the range of 10-100 U per day, such as from 20-100 U per day.

64. The method according to any of the preceding embodiments, wherein said subject receives concomitant treatment with a GLP-1 agonist, such as liraglutide.

65. The method according to any of the preceding embodiments, wherein said subject receives concomitant treatment with liraglutide by injection of a combination product comprising insulin degludec and liraglutide.

66. A kit of parts comprising
    insulin degludec,
    a packaging material, and
    a label or package insert contained within the packaging material indicating that subjects receiving the treatment with insulin degludec can be treated by a method according to any of embodiments 1-65.

67. A kit of parts comprising
    insulin degludec,
    a packaging material, and
    a label or package insert contained within the packaging material indicating that subjects receiving the treatment with insulin degludec can be treated by a method according to any of embodiments 1-65, wherein in such treatment the risk for MACE is lower than compared to corresponding therapy using insulin glargine.

EXAMPLES

List of Abbreviations

MACE: Major adverse cardiovascular event
$HbA_{1c}$: Glycosylated haemoglobin
BMI: Body mass index
N: Number of subjects
CV: Cardiovascular
OAD: Oral antidiabetic drug
TIA: Transient ischaemic attack
CI: Confidence interval
HR: Hazard ratio
CKD-EPI: Chronic Kidney Disease Epidemiology Collaboration MDRD: modification of diet in renal disease
eGFR: Estimated glomerular filtration rate
CVD: Cardiovascular disease
CKD: Chronic kidney disease
NYHA: New York Heart Association
SGLT2: Sodium-Dependent Glucose Transporter type 2
SMPG: Self Monitored Plasma Glucose
MI: Myocardial infarction
UAP: Unstable angina pectoris
ACE: angiotensin converting enzyme
ASA: Acetylsalicylic acid or acetylsalicylate lysine
NS: not significant
AACE: American association of endocrinologists
ADA: American diabetes association
EASD: European association of the study of diabetes
ETD: estimated treatment difference
FPG: fasting plasms glucose
LDL: low density lipoprotein
HDL: high density lipoprotein
VLDL: very-low density lipoprotein
IDeg: Insulin degludec as the product Tresiba®
IDegLira: Combination product containing insulin degludec and liraglutide as active substances (administered as the product Xultophy®)
IGlar: Insulin glargine (Lantus®)

Clinical trial: Materials and Methods

A long-term, multi-centre, multi-national, randomised, double-blind, parallel-group, active comparator-controlled trial with 7637 human subjects was carried out with treatment that would continue until at least 633 positively adjudicated primary cardiovascular events were accrued. This trial concerned incidence of cardiovascular events in adult human subjects with type 2 diabetes that were at high risk for cardiovascular events, including such subjects with existing cardiovascular disease. The primary objective of this trial was to confirm the cardiovascular safety of insulin degludec (Tresiba®) compared to that of insulin glargine (Lantus®). The secondary objective was to assess efficacy of insulin degludec on markers of glycaemic control and to assess safety on other parameters in subjects with type 2 diabetes that were at high risk for cardiovascular events. All trial endpoints were collected and assessed throughout the entire duration of the trial. Subject inclusion and exclusion criteria were as described in Table 1.

TABLE 1

Inclusion and exclusion criteria

| Inclusion Criteria | Exclusion Criteria |
|---|---|
| Type 2 diabetes<br>$HbA_{1c} \geq 7.0\%$ or<br>$HbA_{1c} <7.0\%$ and current insulin treatment corresponding to $\geq 20$ units/day of basal insulin<br>Current treatment with one or more oral or injectable antidiabetic agent(s)<br>Age $\geq 50$ years at screening and at least one of the below conditions:<br>prior myocardial infarction<br>prior stroke or prior transient ischaemic attack (TIA)<br>prior coronary, carotid or peripheral arterial revascularisation<br>>50% stenosis on angiography or other imaging of coronary, carotid or lower extremity arteries<br>history of symptomatic coronary heart disease documented by positive exercise stress test or any cardiac imaging, or unstable angina pectoris with ECG changes<br>asymptomatic cardiac ischemia documented by positive nuclear imaging test or exercise test or dobutamine stress echo<br>chronic heart failure NYHA class II-III<br>chronic kidney disease corresponding to glomerular filtration rate 30-59 mL/min/1.73 m$^2$ per CKD-EPI or<br>Age $\geq 60$ years at screening and at least one of the below risk factors:<br>microalbuminuria or proteinuria<br>hypertension and left ventricular hypertrophy by ECG or imaging<br>left ventricular systolic and diastolic dysfunction by imaging<br>ankle/brachial index <0.9 | An acute coronary or cerebrovascular event in the previous 60 days<br>Planned coronary, carotid or peripheral artery revascularisation<br>Chronic heart failure NYHA class IV<br>Current haemodialysis or peritoneal dialysis or eGFR <30 mL/min/1.73 m$^2$ per CKD-EPI<br>End-stage liver disease, defined as the presence of acute or chronic liver disease and recent history of one or more of the following: ascites, encephalopathy, variceal bleeding, bilirubin $\geq 2.0$ mg/dL, albumin level $\leq 3.5$ g/dL, prothrombin time $\geq 4$ seconds prolonged, international normalised ratio (INR) $\geq 1.7$ or prior liver transplant<br>Current or past (within the last 5 years) malignant neoplasms (except basal cell and squamous cell skin carcinoma)<br>Known or suspected hypersensitivity to trial products or related products<br>Female of child-bearing potential who is pregnant, breast-feeding or intends to become pregnant or is not using adequate contraceptive methods as required by local law or practice<br>Expected simultaneous participation in any other clinical trial of an investigational medicinal product. Participation in a clinical trial with stent(s) is allowed.<br>Receipt of any investigational medicinal product within 30 days before randomisation. Brazil: Receipt of any investigational medicinal product within one year before randomisation unless there is a direct benefit to the subject at the investigator's discretion<br>Current or past (within the last 5 years) malignant neoplasms (except basal cell and squamous cell skin carcinoma)<br>Any condition that in the investigator's opinion would make the subject unable to adhere to the initial trial visit schedule and procedures |

The subject's characteristics, cardiovascular risk profile, cardiovascular medication, and antidiabetic treatment regimens of the randomised subjects at baseline were as shown in Tables 2-5.

TABLE 2

Baseline characteristics

|  | Insulin degludec | Insulin glargine |
|---|---|---|
| Total number of subjects | 3818 | 3819 |
| Male sex, N (%) | 2396 (62.8) | 2382 (62.4) |
| Age, years | 64.9 | 65.0 |
| Diabetes duration, years | 16.6 | 16.2 |
| HbA$_{1c}$, % | 8.44 | 8.41 |
| BMI, kg/m$^2$ | 33.6 | 33.6 |
| Body weight, kg | 96.1 | 96.1 |
| Systolic blood pressure, mmHg | 135.4 | 135.7 |
| Diastolic blood pressure, mmHg | 76.1 | 76.2 |

Full analysis set.
N: Number of subjects,
%: Percentage of subjects relative to the number of randomised subjects.
Demographic information was obtained at the screening visit

TABLE 3

Cardiovascular risk profile at baseline

|  | Insulin degludec | | Insulin glargine | |
|---|---|---|---|---|
| Inclusion criteria | n | % | n | % |
| Total number of subjects | 3818 | | 3819 | |
| Age ≥50 years and established CV or chronic kidney disease | | | | |
| Prior myocardial infarction | 1303 | 34.1 | 1303 | 34.1 |
| Prior stroke or prior TIA | 593 | 15.5 | 649 | 17.0 |
| Prior arterial revascularisation | 1709 | 44.8 | 1662 | 43.5 |
| >50% stenosis on angiography | 960 | 25.1 | 965 | 25.3 |
| Documented history of symptomatic coronary heart disease | 653 | 17.1 | 637 | 16.7 |
| Documented asymptomatic cardiac ischaemia | 170 | 4.5 | 160 | 4.2 |
| Chronic heart failure NYHA II or III | 468 | 12.3 | 487 | 12.8 |
| CKD (eGFR 30-59 mL/min/1.73 m$^2$ per CKD-EPI) | 1197 | 31.4 | 1193 | 31.2 |
| Age ≥60 years and risk factors for CV disease | | | | |
| Microalbuminuria or proteinuria | 391 | 10.2 | 389 | 10.2 |
| Hypertension and left ventricular hypertrophy | 149 | 3.9 | 174 | 4.6 |
| Left ventricular systolic and diastolic dysfunction | 30 | 0.8 | 25 | 0.7 |
| Ankle/brachial index <0.9 | 54 | 1.4 | 63 | 1.6 |

Full analysis set.
N: Number of subjects,
%: Percentage of subjects relative to the number of randomised subjects,
CVD: Cardiovascular disease,
CKD: Chronic kidney disease,
NYHA: New York Heart Association,
eGFR: Estimated glomerular filtration rate,
CKD-EPI: Chronic kidney disease epidemiology collaboration

TABLE 4

Cardiovascular medication at baseline

|  | Insulin degludec | | Insulin glargine | |
|---|---|---|---|---|
|  | n | % | n | % |
| Total number of subjects | 3818 | | 3819 | |
| Antihypertensive therapy | 3559 | 93.2 | 3550 | 93.0 |
| Beta blockers | 2210 | 57.9 | 2190 | 57.3 |
| Calcium channel blockers | 1214 | 31.8 | 1244 | 32.6 |
| ACE inhibitors | 1831 | 48.0 | 1796 | 47.0 |
| Angiotensin receptor blockers | 1289 | 33.8 | 1266 | 33.2 |
| Others | 402 | 10.5 | 375 | 9.8 |
| Diuretics | 1902 | 49.8 | 1914 | 50.1 |
| Loop diuretics | 856 | 22.4 | 882 | 23.1 |
| Thiazides | 887 | 23.2 | 855 | 22.4 |
| Others | 537 | 14.1 | 534 | 14.0 |
| Lipid-lowering drugs | 3147 | 82.4 | 3127 | 81.9 |
| Statins | 3020 | 79.1 | 2982 | 78.1 |
| Fibrates | 425 | 11.1 | 426 | 11.2 |
| Ezetimibe | 175 | 4.6 | 171 | 4.5 |
| Others | 131 | 3.4 | 137 | 3.6 |
| Platelet aggregation inhibitors | 2749 | 72.0 | 2741 | 71.8 |
| Acetylsalicylic acid | 2501 | 65.5 | 2491 | 65.2 |
| Others | 910 | 23.8 | 887 | 23.2 |
| Anti-thrombotic medication | 308 | 8.1 | 289 | 7.6 |

Full analysis set
N: Number of subjects,
%: Percentage of subjects relative to the number of randomised subjects,
ACE: angiotensin converting enzyme,
ASA: Acetylsalicylic acid or acetylsalicylate lysine

TABLE 5

Antidiabetic treatment at baseline

|  | Insulin degludec | | Insulin glargine | |
|---|---|---|---|---|
|  | n | % | n | % |
| Total number of subjects | 3818 | | 3819 | |
| Insulins | | | | |
| Insulin naïve | 604 | 15.8 | 624 | 16.3 |
| Basal insulin only | 1454 | 38.1 | 1440 | 37.7 |
| Basal-bolus insulin (including bolus only and pre-mix) | 1760 | 46.1 | 1755 | 46.0 |
| Antidiabetic treatment (excl. insulins) | | | | |
| Metformin | 2294 | 60.1 | 2270 | 59.4 |
| Sulphonylurea | 1118 | 29.3 | 1111 | 29.1 |
| Alpha glucosidase inhibitors | 63 | 1.7 | 70 | 1.8 |
| Thiazolidinedione | 145 | 3.8 | 123 | 3.2 |
| DPP-4 inhibitors | 463 | 12.1 | 479 | 12.5 |
| GLP-1 receptor agonists | 300 | 7.9 | 307 | 8.0 |
| SGLT-2 inhibitors | 82 | 2.1 | 86 | 2.3 |
| Other | 50 | 1.3 | 68 | 1.8 |

Full analysis set.
N: Number of subjects,
%: Percentage of subjects relative to the number of randomised subjects,
SGLT2: Sodium-Dependent Glucose Transporter type 2.
Others include: glinides, amylin analogues and bromocriptine.

An 18-month recruitment period was planned. For each subject, trial duration was estimated to be maximum 60.5 months: screening up to 2 weeks, randomised treatment up to 59 months (depending on rate of MACE accrual), and a post-treatment follow-up period of 30 days. Subjects were randomised 1:1 in a double-blinded manner to receive blinded insulin degludec or blinded insulin glargine, each added to standard of care. Subjects continued their current antidiabetic therapy except for the basal insulin component (if any), which was replaced by the investigational product. Treatment with bolus insulin was allowed.

Subjects not currently on insulin were to initiate basal insulin at a dose of 10 units OD given between dinner and bedtime. Subjects receiving basal insulin OD were to transfer unit-to-unit from their previous basal insulin dose. Subjects receiving twice-daily (or more) basal insulin transferred to an OD regimen and the pre-trial total basal insulin dose was reduced by 20-30% in accordance with the label for insulin glargine. For subjects receiving premixed/biphasic insulin OD, the basal component was calculated and transferred unit-to-unit to investigational product OD. The bolus insulin component was calculated and transferred unit-to-unit to bolus insulin and given at the most appropriate meal at the investigator's discretion. For subjects receiving premixed/biphasic insulin twice daily (or more), the total basal component was calculated, reduced by 20-30% and transferred to investigational product OD; the bolus component was to be calculated and transferred to insulin aspart and dosed with the most appropriate meals at the investigator's discretion. Subjects treated with bolus insulin as part of their current insulin regimen could be transferred to insulin aspart unit-to-unit from their previous bolus insulin dose, at the investigator's discretion.

Subjects adjusted their basal insulin dose weekly, aiming for a pre-breakfast (fasting) SMPG value of 71-90 mg/dL (4.0-5.0 mmol/L) by using the algorithm in Table 6. The basal dose was adjusted based on the lowest of three pre-breakfast SMPG values, preferably measured two days prior to dose adjustment and on the day of the dose adjustment. No maximum dose was specified. The investigators were to guide the subjects in adjusting their insulin at clinic visits and phone contacts. Investigators and subjects were recommended to follow the basal insulin titration algorithm. Importantly, however, the decision of adjustment of insulin doses was to be based on all available information, such as symptoms of hypoglycaemia and hyperglycaemia, previous responses to dose adjustments and SMPG values other than those required as per protocol.

TABLE 6

Algorithm for adjusting the basal insulin dose

| Lowest of three pre-breakfast SMPG values | | Adjustment of basal insulin |
|---|---|---|
| mmol/L | mg/dL | Units |
| <4.0 | <71 | −2 |
| 4.0-5.0 | 71-90 | No adjustment |
| 5.1-7.0 | 91-126 | +2 |
| >7.0 | >126 | +4 |

Intensification with bolus insulin and other antidiabetic treatments was allowed during the course of the trial. The starting dose of bolus insulin was 4 units per relevant meal. Bolus dose(s) were adjusted weekly based on pre-meal or bedtime SMPG values measured on the three days prior to bolus dose adjustment, aiming for pre-meal or bedtime SMPG values of 71-126 mg/dL (4.0-7.0 mmol/L) by using the algorithm in Table 7. Titration of bolus insulin could also be done based on carbohydrate counting. This was to be done at the investigator's discretion.

TABLE 7

Algorithm for adjusting the bolus insulin dose(s)

| Lowest of three pre-meal or bedtime SMPG values | | Adjustment of bolus insulin |
|---|---|---|
| mmol/L | mg/dL | Units |
| <4.0 | <71 | −2 |
| 4.0-7.0 | 71-126 | No adjustment |
| >7.0 | >126 | +2 |

Subjects received insulin degludec or insulin glargine by subcutaneous administrations once daily in addition to the subject's standard treatment. Basal insulin was injected in the thigh, the upper arm (deltoid area) or the abdominal wall. The formulations were administered in the form of an aqueous solution comprising insulin degludec or insulin glargine, using identical 100 units/mL, 10-mL vials and 1-mL syringes. The aqueous solution of insulin degludec contained 600 nmol/mL insulin degludec, 1.50 mg/mL phenol, 1.72 mg/mL metacresol, 19.6 mg/mL glycerol, 32.7 µg/mL zinc, and had pH 7.6.

Insulin degludec may be prepared as described in WO2005/012347.

The results of this trial may be presented herein as a number or fraction of subjects experiencing an event. Alternatively, the results of this trial may be presented with hazard ratios estimated in a Cox proportional hazard model, which is the standard statistical model used for estimating time to an event. The term "hazard ratio" (also referred to as "HR") as used herein means the instantaneous risk ratio of experiencing an event when administered insulin degludec compared to insulin glargine which are the two treatments in this trial. An upper limit of the 95% confidence interval (CI) for the HR of less than 1.00 means that the estimated treatment ratio between insulin degludec and insulin glargine with respect to the event of interests is statistically significant in favour of insulin degludec on a 5% significance level. A 5% significance level is the standard level for investigating significance in clinical trials.

TABLE 8

First MACE in selected subgroups
Time to first MACE selected from the group
consisting of cardiovascular death, non-fatal MI,
and non-fatal stroke and relevant subgroup hereof

| Factor | Hazard Ratio (95% CI) | Insulin Degludec | | Insulin Glargine | |
|---|---|---|---|---|---|
| | | n | % | n | % |
| First MACE | 0.91 (0.78;1.06) | 325 | 8.5 | 356 | 9.3 |
| Sex | | | | | |
| Male | 0.99 (0.83; 1.20) | 226 | 9.4 | 225 | 9.5 |
| Female | 0.76 (0.59; 0.99) | 99 | 7.0 | 131 | 9.1 |
| Region | | | | | |
| Africa | 0.30 (0.12; 0.77) | 6 | 4.6 | 18 | 14.4 |
| Asia | 0.42 (0.22; 0.81) | 13 | 4.1 | 31 | 9.4 |

Cox proportional hazard model adjusted for treatment. No adjustment for multiple testing.
*: In this table MACE is selected from the group consisting of cardiovascular death, non-fatal stroke, and non-fatal MI.
%: proportion of subjects with a first MACE, as defined, from the subject first follow-up visit to last patient last visit (16 Oct. 2016).
N: number of subjects.

CV Risk Model

For an individual without known cardiovascular disease, the risk of developing cardiovascular disease can be determined for example by using the Framingham General Risk Score, which was developed based on data from the Framingham Heart Study (see Goff et al.: 2013 ACC/AHA Guideline on the Assessment of Cardiovascular Risk A Report of the American College of Cardiology/American Heart Association Task Force on Practice Guidelines, Circulation. 2014; 129[suppl 2]:S49-S73). A high score based on e.g. age, sex, smoking status, cholesterol and blood pressure means that there is a high risk of developing CV disease within the next 10 years.

Based on the DEVOTE trial, a cardiovascular (CV) risk score has been developed for individuals with established cardiovascular risk. This risk score was developed using available medical history, baseline information and cardiovascular events occurring during the trial. The CV risk score is based on baseline information and medical history that significantly predicted cardiovascular events (Table 9). The variables are listed in descending order according to their impact on the overall risk of major adverse cardiovascular events (MACE), here consisting of cardiovascular death, non-fatal myocardial infarction, or non-fatal stroke. The combination of these variables yields an algorithm that can be used to determine the risk of future MACEs and to determine the benefit of being treated with IDeg compared to IGlar.

TABLE 9

Significant predictors for MACE.
Variable

Prior myocardial infarction
LDL/HDL ratio
Prior stroke
Insulin treatment regimen
$HbA_{1c}$ at baseline
eGFR
Hepatic impairment
Smoking status
Age LDL: low-density lipoprotein,
HDL: high-density lipoprotein,
$HbA_{1c}$: glycated haemoglobin A1c,
eGFR: estimated glomerular filtration rate The CV risk score and estimated MACE hazard ratio for CV risk scores by quartiles based on number of events are presented in FIG. 1. The model shows (Table 10) that, for patients who have a high CV risk score, there is a benefit in terms of lower risk of MACE with IDeg compared to IGlar (i.e., hazard ratio IDeg/IGlar <1). This benefit is seen regardless of which of the individual predictors contribute to the high score.

For example, a patient with a prior myocardial infarction and a high LDL/HDL ratio would be expected to have a greater benefit in terms of reduced CV risk when treated with IDeg compared to IGlar. Likewise, a patient treated with basal-bolus insulin who has a high $HbA_{1c}$ would also have a benefit when treated with IDeg.

TABLE 10

Estimated hazard ratio by CV risk score in quartiles.

| CV risk score | N | Events | % | HR | 95% CI |
|---|---|---|---|---|---|
| Very High | 732 | 157 | 21 | 0.67 | (0.49; 0.92) |
| High | 1460 | 170 | 12 | 1.04 | (0.77; 1.41) |
| Moderate | 2351 | 182 | 8 | 0.89 | (0.67; 1.20) |
| Low | 3094 | 172 | 6 | 1.02 | (0.76; 1.37) |

CV: cardiovascular
CI: confidence interval,
N: number of subjects,
HR: hazard ratio In addition to the CV risk score, a number of subgroups in the DEVOTE trial were shown to have a lower risk of MACE with IDeg compared to IGlar. For example, subjects with a BMI ≥30 kg/m² and diastolic blood pressure ≥80 mmHg, and subjects with a diastolic blood pressure ≥80 mmHg who were treated with statins would have a benefit with IDeg compared to IGlar in terms of risk of MACE (Table 11).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

TABLE 11

CV risk score in subgroups with >100 events

| Subgroups | Subjects | Events | Estimate | Lower CI | Upper CI | P-value |
|---|---|---|---|---|---|---|
| Age <65 years AND diastolic blood pressure ≥80 mmHg | 1874 | 146 | 0.64 | 0.46 | 0.89 | 0.01 |
| Age <65 years AND treated with statins | 2837 | 239 | 0.75 | 0.58 | 0.96 | 0.02 |
| Age 65-75 years AND systolic blood pressure <140 mmHg | 1930 | 173 | 0.70 | 0.52 | 0.95 | 0.02 |
| BMI ≥30 kg/m² AND diastolic blood pressure ≥80 mmHg | 2107 | 168 | 0.68 | 0.5 | 0.93 | 0.02 |
| Diastolic blood pressure <90 mmHg AND HDL ≥1.0 mmol/L | 4385 | 365 | 0.80 | 0.65 | 0.98 | 0.03 |
| Diastolic blood pressure ≥80 mmHg AND treated with statins | 2348 | 202 | 0.73 | 0.55 | 0.97 | 0.03 |
| Diastolic blood pressure ≥80 mmHg AND triglycerides >1.7 mmol/L | 1584 | 133 | 0.69 | 0.49 | 0.98 | 0.04 |
| Height <170 cm AND treated with statins | 2972 | 274 | 0.75 | 0.59 | 0.95 | 0.02 |
| Established CV risk[a] AND diastolic blood pressure ≥80 mmHg | 2654 | 242 | 0.76 | 0.59 | 0.98 | 0.04 |
| Established CV risk[a] AND HDL ≥1.0 mmol/L | 4054 | 358 | 0.78 | 0.64 | 0.97 | 0.02 |
| Established CV risk[a] AND pulse ≥70 bpm | 3838 | 375 | 0.80 | 0.65 | 0.98 | 0.03 |
| Non-White AND diastolic blood pressure <90 mmHg | 1613 | 118 | 0.64 | 0.44 | 0.92 | 0.02 |
| Not Hispanic or Latino AND Non-White | 1663 | 124 | 0.64 | 0.45 | 0.92 | 0.02 |
| Not Hispanic or Latino AND triglycerides >1.7 mmol/L | 3073 | 304 | 0.79 | 0.63 | 0.99 | 0.04 |
| Previous smoker AND age <65 years | 1977 | 190 | 0.73 | 0.55 | 0.98 | 0.03 |

TABLE 11-continued

CV risk score in subgroups with >100 events

| Subgroups | Subjects | Events | Estimate | Lower CI | Upper CI | P-value |
|---|---|---|---|---|---|---|
| Previous smoker AND cholesterol ≥3 mmol/L | 3646 | 359 | 0.79 | 0.64 | 0.97 | 0.03 |
| Previous smoker AND diastolic blood pressure ≥80 mmHg | 1641 | 162 | 0.66 | 0.48 | 0.9 | 0.01 |
| Previous smoker AND treated with statins | 3378 | 337 | 0.79 | 0.63 | 0.97 | 0.03 |
| Previous smoker AND triglycerides >1.7 mmol/L | 2076 | 207 | 0.73 | 0.55 | 0.96 | 0.02 |
| Pulse ≥70 bpm AND diastolic blood pressure ≥80 mmHg | 2191 | 190 | 0.74 | 0.56 | 0.99 | 0.04 |
| Pulse ≥70 mmHg AND treated with statins | 3554 | 323 | 0.72 | 0.58 | 0.9 | 0.00 |
| Pulse ≥70 bpm AND triglycerides >1.7 mmol/L | 2282 | 229 | 0.76 | 0.59 | 0.99 | 0.04 |
| Systolic blood pressure <140 mmHg AND HDL ≥1.0 mmol/L | 2920 | 232 | 0.73 | 0.56 | 0.94 | 0.02 |
| Triglycerides >1.7 mmol/L AND HDL ≥1.0 mmol/L | 1885 | 166 | 0.69 | 0.51 | 0.94 | 0.02 |
| Triglycerides >1.7 mmol/L AND treated with statins | 2772 | 271 | 0.78 | 0.61 | 0.99 | 0.04 |

$^a$According to pre-defined criteria.

Example 2

Clinical Trial: Materials and Methods

A 26-week randomised, parallel two-arm, double-blind, multi-centre, multinational, treat-to-target trial in 413 human subjects with type 2 diabetes inadequately controlled with basal insulin and metformin with or without SU or glinides was carried out comparing the efficacy and safety of insulin degludec+liraglutide (Xultophy®, IDegLira) once daily with insulin degludec (Tresiba®, IDeg) once daily both added on to metformin. The primary objective was to confirm superiority of IDegLira vs IDeg in controlling glycaemia in human subjects with type 2 diabetes. The secondary objective was to compare the overall efficacy and safety parameters of IDegLira and IDeg after 26 weeks of treatment. All trial endpoints were collected and assessed throughout the entire duration of the trial. Subject inclusion and exclusion criteria were as described in Table 12.

TABLE 12

Inclusion and exclusion criteria

| Inclusion Criteria | Exclusion Criteria |
|---|---|
| Informed consent obtained before any trial-related activities (trial related activities are any procedure that would not have been performed during the normal management of the subject) Subjects with type 2 diabetes Male or female, age 18 years or above HbA1c 7.5-10.0% (both inclusive) Subjects on stable daily doses for at least 90 days prior to screening of: a. basal insulin e.g.* insulin glargine, insulin detemir, NPH insulin in combination with i. metformin (≥1500 mg or max tolerated dose) or ii. metformin (≥1500 mg or max tolerated dose) and SU (≥ half of the max approved dose according to local label) or iii. metformin (≥1500 mg or max tolerated dose) and glinides (≥ half of the max approved dose according to local label) (* total daily basal insulin dose within the range of 20-40 units. Individual fluctuations of ±10% within the 90 days prior to screening are acceptable) BMI ≥27 kg/m2 Able and willing to perform self-monitoring of plasma glucose according to the protocol, to keep a diabetes diary and to use FlexPen device | Known or suspected hypersensitivity to trial products or related products Previous participation in this trial. Participation is defined as randomised (screening failures are allowed to be re-screened once during the recruitment period) Females of childbearing potential who are pregnant, breast-feeding or intend to become pregnant or are not using adequate contraceptive methods (adequate contraceptive measures as required by local law or practice). US: Acceptable forms of birth control include sexual abstinence; sterilization of either partner; oral, injectable, implant or transdermal hormonal methods; intrauterine or vaginal device or consistent use of proven barrier methods with spermicide use as indicated. Use of any drug (except for basal insulin, metformin, SU and glinides), which in the investigator's opinion could interfere with glucose level (e.g. systemic corticosteroids) Treatment with GLP-1 receptor agonists (e.g. exenatide, liraglutide), dipeptidyl peptidase 4 (DPP-4) inhibitors and/or thiazolidinediones within 90 days prior to screening Subject with a clinically significant, active (during the past 12 months) disease of the gastrointestinal, pulmonary, endocrinological (except for type 2 diabetes), neurological, genitourinary or haematological system (except for conditions associated with type 2 diabetes), that in the opinion of the Investigator, may confound the results of the trial or pose additional risk in administering trial drug The receipt of any investigational product within 30 days prior to screening Impaired liver function, defined as alanine aminotransferase (ALAT) ≥2.5 times upper normal range (UNR) (one retest analysed at the central laboratory within a week from first sample taken is permitted with the result of the last sample being the conclusive) Impaired renal function defined as serum-creatinine ≥133 μmol/L (≥1.5 mg/dL) for males and ≥125 μmol/L (≥1.4 mg/dL) for females, or as allowed according to local contraindications for metformin (one retest analysed at the central laboratory within a week from first sample taken is permitted with the result of the last sample being the conclusive) Screening calcitonin ≥50 ng/L Subjects with personal or family history of medullary thyroid carcinoma (MTC) or multiple endocrine neoplasia type 2 (MEN 2) Cardiac disorder defined as: congestive heart failure (NYHA class III-IV (see Appendix E)), diagnosis of unstable angina pectoris, cerebral stroke and/or myocardial infarction within the last 52 weeks prior to screening and/or planned coronary, carotid or peripheral artery revascularisation procedures Severe uncontrolled treated or untreated hypertension (systolic blood pressure ≥180 mm Hg or diastolic blood pressure ≥100 mm Hg) Proliferative retinopathy requiring acute treatment or maculopathy (macular oedema) according to investigator's opinion Mental incapacity, unwillingness or language barrier precluding adequate understanding of the trial procedure or cooperation with trial site personnel Known or suspected abuse of alcohol or narcotics History of chronic pancreatitis or idiopathic acute pancreatitis |

TABLE 12-continued

Inclusion and exclusion criteria

| Inclusion Criteria | Exclusion Criteria |
|---|---|
| | Cancer (except basal cell skin cancer or squamous cell skin cancer), which in the investigator's opinion could interfere with the results of the trial, or cancer during the 5 past years |

The subject's characteristics at baseline were as shown in Table 13.

TABLE 13

Baseline characteristics

| | IDegLira | IDeg |
|---|---|---|
| Total number of subjects | 199 | 199 |
| Male sex, N (%) | 112 (56.3) | 106 (53.3) |
| Age, years | 56.8 | 57.5 |
| Diabetes duration, years | 10.3 | 10.9 |
| $HbA_{1c}$, % | 8.7 | 8.8 |
| BMI, $kg/m^2$ | 33.6 | 33.8 |
| Body weight, kg | 95.4 | 93.5 |

Eligible subjects were randomised 1:1 to either once daily IDegLira or once daily IDeg, both in combination with metformin. The starting dose was 16 dose steps for IDegLira and 16 units for IDeg and were titrated twice weekly according to the predefined titration algorithm, which was based on FPG levels as seen in table 14. For each subject, the duration of the trial was to be approximately 29 weeks: up to 2 weeks between screening and first treatment, 26 weeks of treatment and at least 1 week of wash-out at the end of the trial. After the trial drug treatment period all subjects were transferred to an alternative antidiabetic therapy at the discretion of the investigator.

The IDegLira dosing unit is defined as a dose step. One (1) IDegLira dose step consists of 1 unit insulin degludec and 0.036 mg liraglutide. Treatment with IDegLira was initiated at 16 dose steps containing 16 units insulin degludec and 0.6 mg liraglutide. Adjustment of the IDegLira dose was performed twice weekly based on the mean of 3 preceding daily fasting SMPG values on 3 consecutive days. Adjustments occurred in 2 dose steps aiming at a fasting glycaemic target of 4.0-5.0 mmol/L (72-90 mg/dL). The maximum allowed dose was 50 dose steps (50 units IDeg/1.8 mg liraglutide). IDeg treatment was initiated with 16 units, and titrated twice weekly to the fasting glycaemic target of 4.0-5.0 mmol/L (72-90 mg/dL) based on the mean fasting SMPG from 3 proceeding measurements as described for IDegLira. The maximum allowed dose was 50 units.

TABLE 14

Adjustment (titration) of IDegLira or IDeg

| Mean fasting plasms glucose | | Dose adjustment |
|---|---|---|
| mmol/L | mg/dL | Units |
| <4.0 | <72 | −2 |
| 4.0-5.0 | 72-90 | No adjustment |
| >5.0 | >90 | +2 |

Subjects received IDegLira or IDeg by subcutaneous administration in addition to metformin. IDegLira or IDeg was injected subcutaneously in the thigh, upper arm (deltoid region) or abdomen once daily preferably at the same time every day. The injection area chosen were to remain unchanged throughout the trial, but rotation within the area was recommended.

The results of the primary endpoint, change in HbA1c, showed superiority of IDegLira over IDeg and was confirmed at equivalent actual insulin doses (45 dose steps for IDegLira/45 units for IDeg), supporting a significant contribution of the liraglutide component to overall glycaemic control. Treatment with IDegLira had a statistically significant favourable effect on FPG, SMPG (mean 9-point SMPG profile and mean 9-point post prandial increments) and body weight when compared to IDeg supporting the contribution of the liraglutide component. Adverse event and tolerability profiles of IDeg were consistent with previous findings.

CV Markers

There was a greater decrease in systolic blood pressure with IDegLira (Table 15), and a small but statistically significant increases in mean heart rate were observed with IDegLira versus IDeg (both $p<0.001$). IDegLira was associated with weight loss versus weight gain with IDeg (estimated treatment difference [ETD] −2.5 kg [−3.2; −1.8] 95% CI $p<0.0001$). Lipid profile improved with IDegLira; total cholesterol and low-density lipoprotein (LDL) cholesterol were significantly lower versus IDeg (Table 16). Additionally, apolipoprotein B (Apo-B) and brain natriuretic peptide (BNP) were significantly lower with IDegLira versus IDeg (estimated treatment ratio [ETR] 0.92 [0.88; 0.95] 95% CI $p<0.0001$ and 0.66 [0.55; 0.79]95% CI $p<0.0001$ respectively), while high-sensitivity C-reactive protein (hsCRP) was similar after 26 weeks of treatment (ETR 0.90 [0.78; 1.04]95% CI p=non-significant).

TABLE 15

Change from baseline in heart rate and blood pressure

| | IDegLira | IDeg | Estimated treatment difference (IDegLira vs IDeg) |
|---|---|---|---|
| Total number of subjects | 199 | 199 | |
| ΔHeart rate, bpm | 2.5 | −0.6 | 2.9 (p < 0.05) |
| ΔSystolic blood pressure, mmHG | −5.4 | −1.7 | −3.7 (p < 0.05) |
| ΔDiastolic blood pressure, mmHG | −1.4 | −0.7 | −0.7 (NS) |

TABLE 16

Change from baseline in lipids

| | IDegLira | | IDeg | |
|---|---|---|---|---|
| Total number of subjects | 199 | | 199 | |
| | Baseline | End of trial | Baseline | End of trial |
| Total cholesterol, mmol/L | 4.6 | 4.3 | 4.6 | 4.5 |
| HDL cholesterol, mmol/L | 1.1 | 1.1 | 1.2 | 1.2 |
| LDL cholesterol, mmol/L | 2.5 | 2.2 | 2.4 | 2.4 |
| VLDL cholesterol, mmol/L | 0.8 | 0.7 | 0.8 | 0.7 |
| Triglycerides, mmol/L | 1.8 | 1.6 | 1.8 | 1.6 |
| Free fatty acids, mmol/L | 0.5 | 0.4 | 0.5 | 0.4 |

In conclusion, people treated with IDegLira had significantly lower systolic blood pressure, lower total cholesterol as well as lower low-density lipoprotein cholesterol (so-called 'bad cholesterol'), and significant weight changes in favour of IDegLira compared to people treated with IDeg. A small but statistically significant increase in heart rate was also observed with IDegLira.

Example 3

Clinical Trial: Materials and Methods

A 26-week multinational, multi-centre, open-label, two-arm parallel, randomised, treat-to-target trial in 557 human subjects with T2DM inadequately controlled on insulin glargine (IGlar, Lantus®) at a daily dose between 20-50 units (both inclusive) in combination with metformin was carried out. The primary objective was to confirm the efficacy of IDegLira in controlling glycaemia in human subjects with T2DM on previous treatment with IGlar. The secondary objective was to compare safety of IDegLira to IGlar after 26 weeks of treatment and to confirm superiority of IDegLira versus IGlar after 26 weeks of treatment on one or more of the following: change from baseline in HbA1c, confirmed hypoglycaemia, change from baseline in body weight. All trial endpoints were collected and assessed throughout the entire duration of the trial. Subject inclusion and exclusion criteria were as described in Table 17.

TABLE 17

Inclusion and exclusion criteria

| Inclusion Criteria | Exclusion Criteria |
|---|---|
| Informed consent obtained before any trial-related activities. Trial-related activities are any procedures that are carried out as part of the trial, including activities to determine suitability for the trial | Known or suspected hypersensitivity to trial products or excipients Previous participation in this trial. Participation is defined as screening. Re-screening is not allowed. Females of child-bearing potential who are pregnant, breast-feeding or intend to become pregnant or are not using adequate contraceptive methods |
| Type 2 diabetes mellitus ≥18 years of age HbA1c 7.0-10.0% [53-86 mmol/mol] (both inclusive) by central laboratory analysis | (adequate contraceptive measures as required by local law or practice). Argentina: Barrier methods (condom or diaphragm) with spermicide; contraceptive pills or intrauterine devices (IUD). Birth control methods will be reimbursed by sponsor. Spain: Acceptable forms of birth control |
| Current treatment with insulin glargine for at least 90 days prior to screening Stable daily dose of insulin glargine between 20 units and 50 units (both inclusive) for at least 56 days prior to screening. Total daily dose should be within the range of 20-50 units, both inclusive, on the day of screening, but individual fluctuations of ±10% within the 56 days prior to screening are acceptable. | (barrier methods, contraceptive pills, IUD, sterilisation, approved hormonal implant, contraceptive patch). Receipt of any investigational medicinal product within 30 days prior to Visit 1 (screening) Any use of oral antidiabetic agents (OADs) (except for metformin) within 90 days prior to Visit 1 (screening) Current use of any drug (except metformin and insulin glargine) or anticipated change in concomitant medication, which in the investigator's opinion could interfere with the glucose metabolism (e.g. systemic corticosteroids) |
| Stable daily dose of metformin (≥1500 mg or max tolerated dose) for at least 90 days prior to screening Body mass index (BMI) ≤40 kg/m2 Able and willing | Previous and/or current treatment with any insulin regimen other than basal insulin, e.g. prandial or pre-mixed insulin (short term treatment due to intercurrent illness including gestational diabetes is allowed at the discretion of the investigator) Previous and/or current treatment with GLP-1 receptor agonists (e.g. exenatide, liraglutide) Impaired liver function, defined as ALAT ≥2.5 times upper normal range (UNR) |

TABLE 17-continued

Inclusion and exclusion criteria

| Inclusion Criteria | Exclusion Criteria |
|---|---|
| to adhere to the protocol including performing self-measured plasma glucose profiles, to keep a trial diary and to use pre-filled pen device. | Impaired renal function defined as serum-creatinine ≥ 133 µmol/L (≥1.5 mg/dL) for males and ≥125 µmol/L (≥1.4 mg/dL) for females, or as allowed according to local contraindications for metformin Screening calcitonin ≥50 ng/L Personal or family history of medullary thyroid carcinoma (MTC) or multiple endocrine neoplasia type 2 (MEN2) Cardiovascular disorders defined as; congestive heart failure [New York Heart Association (NYHA) class III-IV], diagnosis of unstable angina pectoris, cerebral stroke and/or myocardial infarction within the past 26 weeks prior to visit 1 and/or planned coronary, carotid or peripheral artery revascularisation procedures Severe uncontrolled treated or untreated hypertension (systolic blood pressure ≥180 mmHg ordiastolic blood pressure ≥100 mmHg) Argentina: Severe uncontrolled treated or untreated hypertension (defined as systolic blood pressure ≥150 mmHg and/or diastolic blood pressure ≥90 mmHg) Proliferative retinopathy requiring acute treatment or maculopathy (macular oedema), according to the investigator's opinion Subjects with clinically significant, active (during the past 12 months) disease of the gastrointestinal, pulmonary, endocrinological (excluding T2DM), neurological, genitourinary or haematological system, that in the opinion of the investigator may confound the results of the trial or pose additional risk in administering trial drug Mental incapacity, unwillingness or language barrier precluding adequate understanding of the trial procedures or cooperation with the trial personnel Known or suspected abuse of prescription drugs, alcohol or illicit substances History of chronic pancreatitis or idiopathic acute pancreatitis Suffer from a life threatening disease including malignant neoplasms and medical history of malignant neoplasms within the last 5 years (except basal and squamous cell skin cancer) Argentina: Active diabetic ulcer or subjects with a history of diabetic foot (ulcers and/or amputation) in a period of 1 year prior to screening. |

The subject's characteristics at baseline were as shown in table 18.

TABLE 18

Baseline characteristics

| | IDegLira | IGlar |
|---|---|---|
| Total number of subjects | 278 | 279 |
| Male sex, N (%) | 143 (51.4) | 137 (49.1) |
| Age, years | 58.4 | 59.1 |
| Diabetes duration, years | 11.64 | 11.33 |
| HbA$_{1c}$, % | 8.4 | 8.2 |

TABLE 18-continued

Baseline characteristics

|  | IDegLira | IGlar |
| --- | --- | --- |
| BMI, kg/m² | 31.7 | 31.7 |
| Body weight, kg | 88.3 | 87.3 |

Eligible subjects were randomised 1:1 to either once daily IDegLira or once daily IGlar both in combination with metformin The starting dose of IDegLira was 16 dose steps (16 units insulin degludec/0.6 mg liraglutide) and was titrated according to a predefined titration algorithm with a maximum dose of 50 dose steps (50 units insulin degludec/ 1.8 mg liraglutide) as seen in table 19. IGlar was given at a start dose equal to the pre-trial daily dose of IGlar (dose-to-dose switch) and was titrated according to a predefined titration algorithm with no maximum dose.

For each subject, the duration of the trial was to be approximately 29 weeks, consisting of a 2-week screening period, a 26-week treatment period and a follow-up visit 1 week after end of treatment. The trial included a screening visit to assess subjects' eligibility and weekly visits/phone contacts during the 26-week treatment period.

Subjects randomised to treatment with IDegLira discontinued the pre-trial IGlar treatment prior to initiating IDegLira treatment with a start dose of 16 dose steps, equivalent to 16 units insulin degludec and 0.6 mg liraglutide. The maximum allowed dose was 50 dose steps (50 units insulin degludec/1.8 mg liraglutide). Subjects randomised for treatment with IGlar discontinued on the pre-trial, stable IGlar treatment prior to initiating IGlar treatment with a start dose of IGlar equal to the pretrial daily dose (dose-to-dose switch). No predefined maximum dose was specified for IGlar treatment.

Adjustment of the dose of IDegLira and IGlar was to be performed twice weekly based on the mean of 3 preceding daily fasting SMPG values on 3 consecutive days. Adjustments were to occur in increments or decrements of 2 dose steps, aiming at a fasting glycaemic target of 4.0-5.0 mmol/L (71-90 mg/dL), see table 19.

TABLE 19

Adjustment (titration) of IDegLira or IGlar

| Mean of three pre-breakfast SMPG values | | Dose adjustment |
| --- | --- | --- |
| mmol/L | mg/dL | Units |
| <4.0 | <71 | −2 |
| 4.0-5.0 | 71-90 | No adjustment |
| >5.0 | >90 | +2 |

Subjects received IDegLira or IGlar by subcutaneous administration once daily in addition to metformin. IDegLira was to be injected subcutaneously in the thigh, upper arm (deltoid region) or abdomen once daily approximately at the same time every day. The injection area chosen was to remain unchanged throughout the trial, but rotation within the area was recommended. IGlar was to be injected according to the approved label and using the pre-trial dosing time and injection site throughout the trial.

The result of the primary endpoint was confirmed showing superiority of IDegLira vs. IGlar demonstrating a glycaemic benefit of transferring from IGlar to IDegLira treatment when in need of intensification. In addition, the glycaemic benefit of IDegLira was furthermore demonstrated by the proportion of subjects reaching the pre-defined HbA1c targets after 26 weeks of treatment. Statistically significantly more subjects in the IDegLira group compared to the IGlar group reached the ADA and EASD target of HbA1c <7% and the AACE target of HbA1c ≤6.5%. Mean body weight decreased with 1.4 kg in the IDegLira group and increased with 1.8 kg in the IGlar group with an estimated mean treatment difference of −3.20 kg confirming superiority. The proportion of subjects experiencing confirmed hypoglycaemic episodes during the trial was statistically significantly lower in the IDegLira group (28.4%) compared to the IGlar group (49.1%) with an estimated treatment ratio of 0.43 confirming superiority.

CV Markers

There was a greater decrease in systolic blood pressure with IDegLira (Table 20), and small but statistically significant increases in mean heart rate were observed with IDegLira versus IGlar (both p<0.001). IDegLira was associated with weight loss versus weight gain with IGlar (estimated treatment difference [ETD] −3.2 kg [−3.8; −2.6]95% CI p<0.005). Lipid profile improved with IDegLira; total cholesterol and low-density lipoprotein (LDL) cholesterol were significantly lower versus IGlar (Table 21).

TABLE 20

Change from baseline in heart rate and blood pressure

|  | IDegLira | IGlar | Estimated treatment difference (IDegLira vs IGlar) |
| --- | --- | --- | --- |
| Total number of subjects | 278 | 279 | |
| ΔHeart rate, bpm | 3.1 | −0.2 | 3.7 (p < 0.05) |
| ΔSystolic blood pressure, mmHG | −3.7 | −0.2 | −3.6 (p < 0.05) |
| ΔDiastolic blood pressure, mmHG | −0.8 | −1.4 | 0.9 (NS) |

TABLE 21

Change from baseline in lipids

| | IDegLira | | IGlar | |
| --- | --- | --- | --- | --- |
| Total number of subjects | 278 | | 279 | |
| | Baseline | End of trial | Baseline | End of trial |
| Total cholesterol, mmol/L | 4.6 | 4.4 | 4.5 | 4.6 |
| HDL cholesterol, mmol/L | 1.2 | 1.2 | 1.2 | 1.2 |
| LDL cholesterol, mmol/L | 2.5 | 2.3 | 2.4 | 2.5 |
| VLDL cholesterol, mmol/L | 0.8 | 0.7 | 0.8 | 0.8 |
| Triglycerides, mmol/L | 1.7 | 1.6 | 1.7 | 1.7 |
| Free fatty acids, mmol/L | 0.5 | 0.4 | 0.4 | 0.4 |

In conclusion, people treated with IDegLira had significantly lower systolic blood pressure, lower total cholesterol as well as lower low-density lipoprotein cholesterol (so-called 'bad cholesterol'), and significant weight changes in favour of IDegLira compared to people treated with IGlar. A small but statistically significant increase in heart rate was also observed with IDegLira.

The invention claimed is:

1. A method for treating diabetes comprising:
   administration of a basal insulin in a therapeutically effective amount to a subject in need thereof, wherein said subject has a cardiovascular disease or is at risk of developing a cardiovascular disease and wherein said basal insulin is insulin degludec, wherein said method delays or reduces major adverse cardiovascular event (MACE),
wherein said MACE is selected from cardiovascular death, non-fatal myocardial infarction (MI), and non-fatal stroke, and wherein said MACE is reduced from about 5% to about 15% compared to placebo.

2. The method according to claim 1, wherein said subject is a female, has substantially Asian origin, and/or has substantially African origin.

3. The method according to claim 1, wherein said subject has
   (i) one or more vascular disease selected from the group consisting of cardiovascular disease, cerebrovascular disease, peripheral vascular disease, chronic renal failure, and chronic heart failure, and/or
   (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9.

4. The method according to claim 1, wherein said subject has
   Type 2 diabetes, and
   $HbA_{1c} \geq 7.0\%$ or $HbA_{1c} < 7.0\%$ and current insulin treatment corresponding to ≥20 units/day of basal insulin, and
   ongoing treatment with one or more oral or injectable antidiabetic agent(s), and
   Age≥50 years at screening and at least one of the below conditions:
   prior myocardial infarction
   prior stroke or prior transient ischaemic attack (TIA)
   prior coronary, carotid or peripheral arterial revascularisation
   >50% stenosis on angiography or other imaging of coronary, carotid or lower extremity arteries
   history of symptomatic coronary heart disease documented by positive exercise stress test or any cardiac imaging, or unstable angina pectoris with electrocardiogram (ECG) changes
   asymptomatic cardiac ischemia documented by positive nuclear imaging test or exercise test or dobutamine stress echo
   chronic heart failure New York Heart Association Functional Classification (NYHA) class II-III
   chronic kidney disease corresponding to glomerular filtration rate 30-59 mL/min/1.73 m² per Chronic Kidney Disease Epidemiology Collaboration (CKD-EPI) or
   Age≥60 years at screening and at least one of the below risk factors:
   microalbuminuria or proteinuria
   hypertension and left ventricular hypertrophy by ECG or imaging
   left ventricular systolic and diastolic dysfunction by imaging
   ankle/brachial index <0.9.

5. The method according to claim 1, wherein said diabetes is type 2 diabetes.

6. The method according to claim 1, wherein said MACE is selected from cardiovascular death, non-fatal MI, and non-fatal stroke.

7. The method according to claim 1, wherein insulin degludec is administered as a chronic treatment for at least 12 months.

8. The method according to claim 1, wherein said subject is a female.

9. The method according to claim 1, wherein said subject has a BMI of at least 30 kg/m².

10. The method according to claim 1, wherein said subject has a HbA1c of at least 7.0%, such as at least 7.5%, or at least 8.0%.

11. The method according to claim 1, wherein said subject has a HbA1c of at least 7.0% or has a HbA1c less than 7.0% combined with being subject to insulin treatment corresponding to at least 20 units/day of basal insulin.

12. The method according to claim 1, wherein said subject already receives treatment with one or more oral antidiabetic agent(s).

13. The method according to claim 1, wherein said insulin degludec is administered once daily in an amount in the range of 10-100 U per day.

14. The method according to claim 1, wherein the placebo is insulin glargine.

15. The method according to claim 1, wherein said insulin degludec is administered once daily in an amount in the range of 20-100 U per day.

* * * * *

UNITED STATES PATENT AND TRADEMARK OFFICE
CERTIFICATE OF CORRECTION

PATENT NO. : 12,233,114 B2
APPLICATION NO. : 17/667223
DATED : February 25, 2025
INVENTOR(S) : Simon Skibsted et al.

Page 1 of 1

It is certified that error appears in the above-identified patent and that said Letters Patent is hereby corrected as shown below:

In the Claims

At Column 37, Claim number 4, Line number 24, please replace:
"$HBA_{1c} \geq 7.0\%$ or $HBA_{1c} \leq 7.0\%$ and current insulin treat-"
With:
"$HBA1c \geq 7.0\%$ or "$HBA1c \leq 7.0\%$ and current insulin treat-".

Signed and Sealed this
Nineteenth Day of August, 2025

Coke Morgan Stewart
*Acting Director of the United States Patent and Trademark Office*